(12) United States Patent
Hesson et al.

(10) Patent No.: US 8,497,243 B2
(45) Date of Patent: Jul. 30, 2013

(54) METHODS AND COMPOSITIONS USEFUL IN THE TREATMENT OF MUCOSITIS

(75) Inventors: David Paul Hesson, Malvern, PA (US); Michael Scott Kramer, Harleysville, PA (US)

(73) Assignee: Promedior, Inc., Lexington, MA (US)

(*) Notice: Subject to any disclaimer, the term of this patent is extended or adjusted under 35 U.S.C. 154(b) by 1029 days.

(21) Appl. No.: 12/217,614

(22) Filed: Jul. 7, 2008

(65) Prior Publication Data

US 2009/0074754 A1    Mar. 19, 2009

Related U.S. Application Data

(60) Provisional application No. 60/958,634, filed on Jul. 6, 2007, provisional application No. 60/961,343, filed on Jul. 20, 2007.

(51) Int. Cl.
*A61K 38/17* (2006.01)
*C07K 14/47* (2006.01)

(52) U.S. Cl.
CPC .................. *A61K 38/1738* (2013.01)
USPC ....... 514/13.2; 514/13.5; 514/19.2; 514/19.3; 514/20.9; 514/21.2; 530/350; 530/380; 530/395

(58) Field of Classification Search
USPC .................. 514/13.2, 13.5, 19.2, 19.3, 20.9, 514/21.2; 530/350, 380, 395
See application file for complete search history.

(56) References Cited

U.S. PATENT DOCUMENTS

| | | | |
|---|---|---|---|
| 4,233,969 A | 11/1980 | Lock et al. | |
| 4,782,014 A | 11/1988 | Serban et al. | |
| 5,092,876 A | 3/1992 | Dhawan et al. | |
| 5,591,709 A | 1/1997 | Lindenbaum | |
| 5,654,186 A | 8/1997 | Cerami et al. | |
| 5,698,589 A | 12/1997 | Allen | |
| 5,750,345 A | 5/1998 | Bowie | |
| 5,804,446 A | 9/1998 | Cerami et al. | |
| 5,846,796 A | 12/1998 | Cerami et al. | |
| 5,989,811 A | 11/1999 | Veltri et al. | |
| 6,037,458 A | 3/2000 | Hirai et al. | |
| 6,054,121 A | 4/2000 | Cerami et al. | |
| 6,071,517 A | 6/2000 | Fanger et al. | |
| 6,126,918 A | 10/2000 | Pepys et al. | |
| 6,174,526 B1 | 1/2001 | Cerami et al. | |
| 6,365,570 B1 | 4/2002 | Van Kessel et al. | |
| 6,406,698 B1 | 6/2002 | Svehang et al. | |
| 6,537,811 B1 | 3/2003 | Freier | |
| 6,600,019 B2 | 7/2003 | Prayaga et al. | |
| 6,660,843 B1 | 12/2003 | Feige et al. | |
| 6,872,541 B2 | 3/2005 | Mills | |
| 2002/0058284 A1 | 5/2002 | Winkel | |
| 2003/0003567 A1 | 1/2003 | Barber et al. | |
| 2003/0022245 A1 | 1/2003 | Mills | |
| 2003/0162180 A1 | 8/2003 | Pricop | |
| 2004/0068095 A1 | 4/2004 | Shimkets et al. | |
| 2004/0121343 A1 | 6/2004 | Buechler et al. | |
| 2005/0182042 A1 | 8/2005 | Feldman et al. | |
| 2005/0238620 A1 | 10/2005 | Gomer et al. | |
| 2007/0048855 A1 | 3/2007 | Gamez et al. | |
| 2007/0065368 A1 | 3/2007 | Gomer et al. | |
| 2010/0317596 A1 | 12/2010 | Willett et al. | |

FOREIGN PATENT DOCUMENTS

| | | |
|---|---|---|
| WO | WO-92/21364 | 12/1992 |
| WO | WO 94/27640 | 12/1994 |
| WO | WO-95/05394 | 2/1995 |
| WO | WO 95/33454 | 12/1995 |
| WO | WO-97/26906 | 7/1997 |
| WO | WO-99/41285 | 8/1999 |
| WO | WO-01/74300 | 10/2001 |
| WO | WO-03/031572 | 4/2003 |
| WO | WO-03/097104 | 11/2003 |
| WO | WO-2004/016750 | 2/2004 |
| WO | WO-2004/058292 | 7/2004 |
| WO | WO-2004/059318 | 7/2004 |
| WO | WO-2004/076486 | 9/2004 |
| WO | WO-2005/110474 | 11/2005 |
| WO | WO-2005/115452 | 12/2005 |
| WO | WO-2006/002438 | 1/2006 |
| WO | WO-2006/002930 | 1/2006 |
| WO | WO-2006/028956 | 3/2006 |
| WO | WO-2007/047207 | 4/2007 |
| WO | WO-2007/047796 | 4/2007 |
| WO | WO-2008/070117 | 6/2008 |
| WO | WO-2009/009034 | 1/2009 |

OTHER PUBLICATIONS

Bharadwaj, D. et al., The Journal of Immunology, 166: 6735-6741, 2001.*
Castano, A.P., et al. Sci. Transl. Med., 1(5):1-26, 2009.*
Murray, L., A., et al. PLoS ONE, 5(3): 1-9, 2010.*
Abe, R., et al., "Peripheral Blood Fibrocytes: Differentation Pathway and Migration to Wound Sites," The Journal of Immunology, 166(12):7556-7562 (2001).
Aiba, S., et al., "Immunoglobulin-Producing Cells in Plasma Cell Orificial Mucositis," Journal of Cutaneous Pathology, 16(4):207-210 (1989).
Alles, V. V., et al., "Inducible expression of PTX3, a new member of the pentraxin family, in human mononuclear phagocytes," Blood, 84(10):3483-3493 (1994).
Ashcroft, T., et al., "Simple Method of Estimating Severity of Pulmonary Fibrosis on a Numerical Scale," J Clin Pathol, 41(4):467-470 (1988).
Ashikawa, K., et al., "Piceatannol Inhibits TNF-Induced NF-kB Activation and NF-kB-Mediated Gene Expression Through Suppression of IkBα Kinase and p65 Phosphorylation," The Journal of Immunology, 169(11):6490-6497 (2002).
Azuma, H., et al., "Superagonistic CD28 Antibody Induces Donor-Specific Tolerance in Rat Renal Allografts," American Journal of Transplatation, 8(10):2004-2014 (2008).
Bain, J., et al., "The Specificities of Protein Kinase Inhibitors: An Update," Biochem. J, 371(Pt 1):199-204 (2003).
Barna, B. P., et al., "Activation of Human Monocyte Tumoricidal Activity by C-Reactive Protein," Cancer Research, 47(5):3959-3963 (1987).

(Continued)

*Primary Examiner* — Misook Yu
*Assistant Examiner* — Anne Holleran
(74) *Attorney, Agent, or Firm* — Ropes & Gray LLP

(57) ABSTRACT

In certain aspects, the present invention provides compositions and methods for treating mucositis.

24 Claims, 11 Drawing Sheets

OTHER PUBLICATIONS

Bharadwaj, D., et al., "Serum Amyloid P Component Binds to Fcγ Receptors and Opsonizes Particles for Phagocytosis," The Journal of Immunology, 166(11):6735-6741 (2001).

Bharadwaj, D., et al., "The Major Receptor for C-Reactive Protein on Leukocytes Is Fcγ Receptor II," The Journal of Experimental Medicine, 190(4):585-590 (1999).

Bickerstaff, M. C. M., et al., "Serum Amyloid P Component Controls Chromatin Degration and Prevents Antinuclear Autoimmunity," Nature Medicine, 5(6):694-697 (1999).

Biro, E., et al., "Activated Complement Components and Complement Activator Molecules on the Surface of Cell-Derived Microparticles in Patients with Rheumatoid Arthritis and Healthy Individuals," Annals of the Rheumatic Diseases, 66(8):1085-1092 (2007).

Bodman-Smith, K. B., et al., "C-Reactive Protein-Mediated Phagocytosis and Phospholipase D Signalling Through the High-Affinity Receptor for Immunoglobulin G (FcγRI)," The Journal of Immunology, 107(2):252-260 (2002).

Brown, E. J., "The Role of Extracellular Matrix Proteins in the Control of Phagocytosis," Journal of Leukocyte Biology, 39(5):579-591 (1986).

Brown, M. R., et al., "Receptor-Ligand Interactions Between Serum Amyloid P Component and Model Soluble Immune Complexes," The Journal of Immunology, 151(4):2087-2095 (1993).

Bucala, R., et al., "Circulating Fibrocytes Define a New Leukocyte Subpopulation That Mediates Tissue Repair," Molecular Medicine, 1(1):71-81 (1994).

Cappiello, M. G., et al., "Suppression of IL-12 Transcription in Macrophages Following Fcγ Receptor Ligation," the Journal of Immunology, 166(7):4498-4506 (2001).

Castano, A. P., et al., Serum Amyloid P Inhibits Fibrosis Through FcγR-Dependent Monocyte-Macrophage Regulation in VivoSci. Transl. Med. 1(5):1-26 (2009).

Chen, J., et al., "Platelet FcγRIIA His131Arg Polymorphism and Platelet Function: Antibodies to Platelet-Bound Fibrinogen Induce Platelet Activation," Journal of Thrombosis and Haemostasis, 1(2):355-362 (2003).

Chesney, J., et al., "Peripheral Blood Fibrocytes: Mesenchymal Precursor Cells and the Pathogenesis of Fibrosis," Curr.Rheumatol.Rep, 2(6):501-505 (2000).

Chesney, J., et al., "Regulated Production of Type I Collagen and Inflammatory Cytokines by Peripheral Blood Fibrocytes," The Journal of Immunology, 160(1):419-425 (1998).

Chesney, J., et al., "The Peripheral Blood Fibrocyte is a Potent Antigen-Presenting Cell Capable of Priming Naive T Cells in Situ," Journal of Immunology, 94(12):6307-6312 (1997).

Chi, M., et al., "C-Reactive Protein Induces Signaling Through FcγRIIa on HL-60 Granulocytes," The Journal of Immunology, 168:1413-1418 (2002).

Christner, R. B., et al., "Binding of Human Serum Amyloid P-Component to Phosphocholine", Archives of Biochemistry and Biophysics, 314(2):337-343 (1994).

Clark, R. A. F., "Fibrin and Wound Healing," Annals New York Academy of Sciences 936:355-367 (2001).

Crouch, E., "Patholbiology of Pulmonary Fibrosis," Am J Physiol Lung Cell Mol Physiol, 259(4 Pt 1):L159-L184 (1990).

D'Andrea, A., et al., "Stimulatory and Inhibitory Effects of Interleukin (IL)-4 and IL-13 on the Production of Cytokines by Human Peripheral Blood Mononuclear Cells: Priming for IL-12 and Tumor Necrosis Factor α Production," J Exp Med, 181(2):537-546 (1995).

Daëron, M., "Fc Receptor Biology," Annual Review of Immunology 15:203-234 (1997).

Daëron, M., "Structural Bases of FcγR Functions," Int Rev Immunol. 16(1-2):1-27 (1997).

De Beer, F. C., et al., "Fibronectin and C4-Binding Protein are Selectively Bound by Aggregated Amyloid Component", J Exp Med., 154(4):1134-1149 (1981).

De Beer, F. C., et al., "Isolation and Characterization of C-Reactive Protein and Serum Amyloid P Component in the Rat," Immunology 45(1):55-70 (1982).

De Beer, F. C., et al., "Isolation of Human C-Reactive Protein and serum Amyloid P Component," Journal of Immunological Methods, 50(1):17-31 (1982).

de Haas, C. J. C., et al., "A Synthetic Lipopolysaccharide-Binding Peptide Based on Amino Acids 27-39 of Serum Amyloid P Component Inhibits Lipopolysaccharide-Induced Responses in Human Blood," The Journal of Immunology, 161(7):3607-3615 (1998).

De Paepe, et al., "Hydrogels Based on Agarose and Agarose/Gelatin Blends", International Journal of Artificial Organs, vol. 24, No. 8, p. 543, XP009108972 and XXVIII Congress of the European Society for Artificial Organs on Bridging the Interdisciplinarity; Gent, Belgium; Sep. 22-25, 2001.

Du Clos, T. W., "C-Reactive Protein Reacts With the U1 Small Nuclear Ribonucleoprotein," The Journal of Immunology, 143(8):2553-2559 (1989).

Du Clos, T. W., et al., "Reply to Human C-reactive protein does not bind to fc gamma RIIa on phagocytic cells," The Journal of Clinical Investigation, vol. 107(5):643 (2001).

Duchemin, A. M., et al., "Association of Non-Receptor Protein Tyrosine Kinases with the Fc Gamma RI/Gamma-Chain Complex in Monocytic Cells," The Journal of Immunology, 158(2):865-871 (1997).

Emsley, J., et al., "Structure of Pentameric Human Serum Amyloid P Component," Nature 367(6461):338-345 (1994).

Flesch, B. K., et al., "The FCGR2A—Arg131 Variant is no Major Mortality Factor in the Elderly—Evidence From a German Centurian Study," International Journal of Immunogenetics, 33(4):277-279 (2006).

Garden, A. S., et al., "Head and Neck Radiation and Mucositis," Current Opinion in Supportive and Palliative Care. 1(1):30-34 (2007).

Gewurz, H., et al., "Structure and Function of the Pentraxins," Current Opinion in Immunology, 7(1):54-64 (1995).

Ghazizadeh, S., et al., "Physical and Functional Association of Src-Related Protein Tyrosine Kinases with FcγRII in Monocytic THP-1 Cells," Journal of Biological Chemistry, 269(12):8878-8884 (1994).

Giorgini, A., et al., "Blockade of Chronic Graft-Versus-Host Disease by Alloantigen-induced CD4+CD25+Foxp3+ Regulatory T Cells in Nonlymphopenic Hosts," Journal of Leukocyte Biology, 82(5):1053-1061 (2007).

Gregory, S. G., et al., "The DNA Sequence and Biological Annotation of Human Chromosome 1", Nature 441(7091):315-321 (2006).

Guyre, C. A., et al., "Receptor Modulation by FcγRI-Specific Fusion Porteins is Dependent on Receptor Number and Modified by IgG," The Journal of Immunology, 167(11):6303-6311 (2001).

Hamazaki, Hideaki, "Structure and significance of N-linked sugar unit of human serum amyloid P component," Bichimica et Biophysica Acta, 1037(3):435-438 (1990).

Harris, J. M., et al., "Pegylation A Novel Process for Modifying Pharmacokinetics," Clin. Pharmacokinetics, 40(7):539-551 (2001).

Hartlapp, I., et al., "Fibrocytes Induce an Angiogenic Phenotype in Cultured Endothelial Cells and Promote Angiogenesis in Vivo," The FASEB Journal, 15(12):2215-2224 (2001).

Heegaard, N. H. H., et al., "Ligand-Binding Sites in Human Serum Amyloid P Component," Eur. J. Biochem. 239(3):850-856 (1996).

Hicks et al., "Serum amyloid P component binds to histones and activates the classical complement pathway", The Journal of Immunology, 149:3689-3694 (1992).

Hind, C. R. K., et al., "Human Serum Amyloid P Component, a Circulating Lectin with Specificity for the Cyclic 4,6-Pyruvate Acetal of Galactose: Interactions with Various Bacteria", Biochem.J., 225(1):107-111 (1985).

Hind, C. R., et al, "Binding specificity of serum amyloid P-component for the pyruvate acetal of galactose," Journal of Experimental Medicine, 159(4):1058-1069 (1984).

Hohenester, E., et al., "Crystal Structure of a Decameric Complex of Human Serum Amyloid P Component with Bound dAMP", J. Mol. Biol. 269(4):570-578 (1997).

Huang, Z. Y., et al., "The Monocyte Fcγ Receptors FcγRI/γ and FcγRIIA Differ in their Interaction with Syk and with Src-Related Tyrosine Kinases," J Leukoc Biol 76(2):491-499 (2004).

Hundt, M., et al., "Treatment of Acute Exacerbation of Systemic Lupus Erythematosus with High-Dose Intravenous Immunoglobulin," Rheumatology (Oxford), 39(11):1301-1302 (2000).

Hutchinson, W. L., et al., "Human Serum Amyloid P Component is a Single Uncomplexed Pentamer in Whole Serum," Molecular Medicine, 6(6):482-493 (2000).

Janeway, et al., Immunobiology, 3rd edition, Garland Publishing, pp. 3:1-3:11 (1997).

Junqueira, L. C., et al., "Picrosirius Straining Plus Polarization Microscopy, A Specific Method for Collagen Detection in Tissue Sections," Histochem. J, 11(4):447-455 (1975).

Kessel, A., et al., Intravenous Immunoglobulin Therapy Affects T Regulatory Cells by Increasing Their Suppressive Function, The Journal of Immunology, 179(8):5571-5575 (2007).

Kiernan, U. A., et al., "Proteomic Characterization of Novel Serum Amyloid P Component Variants from Human Plasma and Urine," Proteomics 4(6):1825-1829 (2004).

Kisseleva, T., et al., "Bone Marrow-Derived Fibrocytes Participate in Pathogenesis of Liver Fibrosis," Journal of Hepatology, 45(3):429-438 (2006).

Kivela-Rajamaki, M. J., et al., "Laminin-5-γ2-chain and collagenase-2 (MMP-8) in Human Peri-Implant Sulcular Fluid," Clin. Oral Implants Res., 14(2):158-165 (2003).

Kolstoe et al., "Molecular dissection of Alzheimer's disease neuropathology by depletion of serum amyloid P component", *PNAS*, 106(18):7619-7623 (2009).

Korade-Mirnics, Z., et al., "Src Kinase-Mediated Signaling in Leukocytes," J Leukoc Biol., 68(5):603-613 (2003).

Kucuk, H. F., et al., "Effect of a Selective Cyclooxygenase-2 Inhibitor on Renal Scarring," European Surgical Research, 38(5):451-457 (2006).

Lai, J. Y., et al., "Potent Small Molecule Inhibitors of Spleen Tyrosine Kinase (Syk)," Bioorganic & Medicinal Chemistry Letters, 13(18):3111-3114 (2003).

Lei, K. K., et al., "Genomic DNA Sequence for Human C-Reactive Protein," J. Biol. Chem. 260(24):13377-13383 (1985).

Lindenbaum, E. S., et al., "Serum-Free Cell Culture Medium Induces Acceleration of Wound Healing in Guinea-Pigs," Burns, 21(2):110-115 (1995).

Liu, T., et al., "Human Plasma N-Glycoproteome Analysis by Immunoaffinity Subtraction, Hydrazide Chemistry and Mass Spectrometry," J. Proteome Res., 4(6):2070-2080 (2005).

Lu, J., et al., "Structural Recognition and Functional Activation of FcγR by Innate Pentraxins," Nature, 456(7224):989-992 (2008).

Majno, G., "Chronic Inflammation: Links With Angiogenesis and Wound Healing," American Journal of Pathology, 153(4):1035-1039 (1998).

Mantzouranis, E. C., et al., "Human Serum Amyloid P Component, cDNA Isolation, Complete Sequence of Pre-Serum Amyloid P Component, and Localization of the Gene to Chromosome 1," The Journal of Biological Chemistry, 260(12):7752-7756 (1985).

Marnell, L. L., et al., "C-Reactive Protein Binds to FcγRI in Transfected COS Cells," The Journal of Immunology, 155(4):2185-193 (1995).

Metz, C. N., "Fibrocytes: A Unique Cell Population Implicated in Wound Healing," Cell. Mol. Life Sci., 60(7):1342-1350 (2003).

Mold, C., et al., "Serum Amyloid P Component and C-Reactive Protein Mediate Phagocytosis Through Murine FcγRs," The Journal of Immunology, 166(2):1200-1205 (2001).

Moore, B. B., et al., "CCR2-Mediated Recruitment of Fibrocytes to the Alveolar Space After Fibrotic Injury," American Journal of Pathology, 166(3):675-684 (2005).

Mori, L., et al., "Fibrocytes Contribute to the Myofibroblast Population in Wounded Skin and Originate From the Bone Marrow," Exp Cell Res., 304(1):81-90 (2005).

Mortensen, R. F., et al., "Regulation of phagocytic leukocyte activities by C-reactive protein," Journal of Leukocyte Biology, 67(4):495-500 (2000).

Murphy, T. M., et al., "Extrahepetic Transcription of Human C-Reactive Protein," Journal of Experimental Medicine, 73(2):495-498 (1991).

Murray, L. A., et al., "Serum Amyloid P Therapeutically Attenuates Murine Bleomycin-induced Pulmonary Fibrosis Via Its Effects on macrophages," PLoS, 5(3):e9683 (2010).

Ohnishi, S. et al., "Isolation and Characterization of the Complete Complementary and Genomic DNA Sequences of Human Serum Amyloid P Component," J. Biochem, 100(4):849-858 (1986).

Oliveira, E. B., et al., "Primary Structure of Human C-Reactive Protein," The Journal of Biological Chemistry, 254(2):489-502 (1979).

Oriente, A., et al., "Interleukin-13 Modulates Collagen Homeostasis in Human Skin and Keloid Fibroblasts," The Journal of Pharmacology and Experimental Therapeutics, 292(3):988-994 (2000).

Osmand, A. P., et al., Partial Amino-Acid Sequences of Human and Rabbit C-Reactive Proteins: Homology with Immunoglobulins and Histocompatibility AntigensProc. Natl. Acad. Sci. U.S.A., 74(3):1214-1218 (1977).

Pachence, J., et al., "Tissue-Activated Delivery—Novel Methods for Site-Directed Drug Delivery," Drug Delivery Technology, 3(1):40-45 (2003).

Painter, R. H., "Evidence that C1t (amyloid P-component) is not a subcomponent of the first component of complement (CI)"; J. Immunol., 119(6):2203-2205 (1977).

Paul, William E., M.D., editor, Fundamental Immunology, 3d ed. Raven Press, p. 242 (1993).

Pepys et al., Glycobiology of Human Serum Amyloid P Component Amyloid Amyloidosis, *Proc. Int. Symp. Amyloidosis*, pp. 177-179 (1994).

Pepys, et al., "Targeted pharmacological depletion of serum amyloid P component for treatment of human amyloidosis", *Nature*, 471:254-259 (2002).

Pepys, et al., Human serum amyloid P component is an invariant constituent of amyloid deposits and has a uniquely homogeneous glycostructure, PNAS, 91:5206-5606 (1994).

Pepys, M. B., "Isolation of serum amyloid P-component (Protein SAP) in the Mouse," Immunology, 37(3):637-641 (1979).

Pepys, M. B., et al., "Amyloid P Component. A Critical Review," Amyloid: Int. J. Exp. Invest., 4(4):274-295 (1997).

Pepys, M. B., et al., "Serum Amyloid P Component is the Major Calcium-Dependent Specific DNA Binding Protein of Serum," Biochemical and Biophysical Research Communications, 148(1):308-313 (1987).

Philips, R. J., et al., "Circulating Fibrocytes Traffic to the Lungs in Response to CXCL 12 and Mediate Fibrosis," The Journal of Clinical Investigation, 114(3):438-446 (2004).

Pilling, D. et al., "Inhibition of Fibrocyte Differentiation by Serum Amyloid P.," The Journal of Immunology, 17(10):5537-5546 (2003).

Pilling, D., et al., "Aggregated IgG Inhibits the Differentation of Human Fibrocytes," Journal of Leukocyte Biology, 7996):1242-1251 (2006).

Pilling, D., et al., "Reduction of Bleomycin-Induced Pulmonary Fibrosis by Serum Smyloid P," The Journal of Immunology, 179(6):4035-4044 (2007).

Pontet, M., et al., "One step preparation of both human C-reactive protein and Cit," FEBS Letters, 88(2):172-175 (1978).

Portolano et al., Lack of Promiscuity in Autoantigen-Specific H and L Chain Combinations as Revealed by Human Hand L Chain "Roulette" J. Immunol., 150(3):880-887 (Feb. 1, 1993).

Potempa, L. A., et al., "Effect of Divalent Metal Ions and pH Upon the Binding Reactivity of Human Serum Amyloid P Component, a C-Reactive Protein Homologue, for Zymosan," The Journal of Biological Chemistry, 260(22):12142-12147 (1985).

Prelli, F., et al., "The Primary Structure of Human Tissue Amyloid P Component From A Patient with Primary Idiopathic Amyloidosis," The Journal of Biological Chemistry, 260(24):12895-12898 (1985).

Quan et al., "The role of circulating fibrocytes in fibrosis" Current Rheumatology Reports. 8(2): 145-150 (2006).

Rudikoff et al., "Single amino acid substitution altering antigen-binding specificity." Proc Natl Acad Sci USA, 79(6):1979-1983 (Mar. 1982).

Russo, F. P., et al., "Liver Fibrosis; Bone Marrow Functionality Contributes to Liver Fibrosis," Gastroenterology Week Jul. 31, 2006, 130(6):83-84.

Sada, K., et al., "Structure and Function of Syk Protein-Tyrosine Kinase," J Biochem, 130(2):177-186 (2001).
Saeland, E., at al., "Human C-reactive Protein Does not Bind to FcγRIIa on Phagocytic Cells," The Journal of Clinical Investigation, 107(5):641-643 (2001).
Sawada et al., "The Ace Inhibitor, Quinapril, Ameliorates Peritoneal Fibrosis in An Encapsulating Peritoneal Sclerosis Model in Mice" Pharmacological Research. 46(6): 505-510 (2002).
Schmidt, M., et al., "Identification of Circulating Fibrocytes as Precursors of Bronchial Myofibroblasts in Asthma," The Journal of Immunology, 171(1):380-389 (2003).
Shoenfeld, Y., et al., The mosaic of Autoimmunity: Prediction, Autoantibodies, and Therapy in Autoimmune Diseases—2008, Israel Medical Association Journal, 10(1)1 3-19 (2008).
Shrive, A. K., et al., "Three Dimensional Structure of Human C-Reactive Protein," Nature Structural Biology, 3(4):346-354 (1996).
Siebert et al., "Effect of enzymatic desialylation of human serum amyloid P component on surface exposure of laser photo CIDNP (chemically induced dynamic nuclear polarization)—reactive histidine, tryptophan and tyrosine residues," *FEBS Letters*, 371(1):13-6 (1995).
Sjoblom, T., et al., "The Consensus Coding Sequences of Human Breast and Colorectal Cancers," Science, 314(5797):268-274 (2006).
Srinivasan, N., et al., "Comparative Analyses of Pentraxins: Implications for Protomer Assembly and Ligand Binding," Structure, 2(11):1017-1027 (1994).
Steel, D. M., et al., "The Major Acute Phase Reactants: C-Reactive Protein, Serum Amyloid P Component and Serum Amyloid A Protein," Immunology Today, 15(2):81-88 (1994).
Stein, M. P., et al., "C-reactive Protein Binding to FcγRIIa on Human Monocytes and Neutrophils is Allele-Specific," The Journal of Clinical Investigation, 105(3):369-376 (2000).
Su, L., et al., "Distinct Mechanisms of STAT Phosphorylation Via the Interferon-Alpha/Beta Receptor, Selective Inhibition of STAT3 and STAT5 by Piceatannol," Journal of Biological Chemistry 275(17):12661-12666 (2000).
Sutterwala, F. S., et al., "The Taming of IL-12 Suppressing the production of Proinflammatory Cytokines," Journal of Leukocyte Biology, 65(5):543-551 (1999).
The MGC Project Team, "The Status, Quality, and Expansion of the NIH Full-Length cDNA Project: The Mammalian Gene Collection (MGC)," Genome Research, 14(10B):2121-2127 (2004).
Thompson, A. R., et al., "Human Plasma P Component: Isolation and Characterization," Biochemistry, 17(20):4304-4311 (1978).
Thompson, D., et al., "The Physiological Structure of Human C-Reactive Protein and its Complex with Phosphocholine", Structure, 7(2):169-177 (1999).
Thomson, C. W., et al., "Lentivirally Transduced Recipient-Derived Cells to Ex Vivo Expand Functional FcRγ-Sufficient Double-Negative Regulatory T cells," Molecular Therapy, 15(4):818-824 (2007).
Toubi, E., et al., "High Dose Intravenous Immunoglobulins: An Option in the Treatment of Systemic Lupus Erythematosus," Human Immunology, 66(4):395-402 (2005).
Tridandapani, S., et al., "Regulated Expression and Inhibitory Function of FcgammaRIIb in Human Monocytic Cells," Journal of Biological Chemistry, The American Society for Biochemistry and Molecular Biology, Inc, 277(7):5082-5089 (2002).
Trinchieri, G., Interleukin-12 and the Regulation of Innate Resistance and Adaptive Immunity, Nature Reviews Immunology, 3(2):133-146 (2003).
Tucci, A., et al., "Biosynthesis and Postsynthetic Processing of Human C-Reactive Protein," The Journal of Immunology, 131(5):2416-2419 (1983).
Turner, M., et al., "Tyrosine Kinase SYK: Essential Functions for Immunoreceptor Signalling," Immunology Today, 21(3):148-154 (2000).

Underwood, D. C., et al., SB 239063, "A p38 MAPK Inhibitor, reduces Neutrophilia, Infamatory Cytokines, MMP-9, and Fibrosis in Lung," Am J Physiol Lung Cell Mol Physiol, 279:L895-L902 (2000).
Volanakis, J.E., "Human C-Reactive Protein: Expression, Structure, and Function," Molecular Immunology, 38(2-3):189-197 (2001).
Whitehead, A. S., et al., "Isolation of Human C-Reactive Protein Complementary DNA and Localization of the Gene to Chromosome 1," Science, 221(4605):69-71 (1983).
Woo, P., et al., "Characterization of Genomic and Complementary DNA Sequence of Human C-Reactive Protein, and Comparison with the Complementary DNA Sequence of Serum Amyloid P Component," The Journal of Biological Chemistry, 260(24):13384-13388 (1985).
Wynn, T. A., "IL-13 Effector Functions," Annu Rev Immunol., 2:425-456 (2003).
Yang, L., et al., "Peripheral Blood Fibrocytes From Burn Patients: Identification and Quantification of Fibrocytes in Adherent Cells Cultured From Peripheral Blood Mononuclear Cells," Laboratory Investigation, 82(9):1183-1192 (2002).
Yang, L., et al., "Identification of Fibrocytes in Postburn Hypertrophic Scar," Wound Repair and Regeneration, 13(4):398-404 (2005).
Zahedi K., "Characterization of the Binding of Serum Amyloid P To Type IV Collagen," The Journal of Biological Chemistry, 271(25):14897-14902 (1996).
Zahedi, K., "Characterization of the Binding of Serum Amyloid P To Laminin," The Journal of Biological Chemistry, 272(4):2143-2148 (1997).
Zhang, R., et al., "C-reactive Protein Impairs Human CD14(+) Monocyte-Derived Dendritic Cell Differentiation, Maturation and Function," European Journal of Immunology, 36(11):2993-3006 (2006).
Zheng, J., et al., "Piceatannol, a Stilbene Phytochemical, Inhibits Mitochondrial FOF1-ATPase Activity by Targeting the FI Complex," Biochemical and Biophysical Research Communications, 261(2):499-503 (1999).
Agostini, et al., "Chemokine/Cytokine Cocktail in Idiopathic Pulmonary Fibrosis," Proc. Am. Thorac. Soc., 3(4):357-363 (2006).
Booth, D. R., et al., "Analysis of autoaggregation and ligand binding sites of serum amyloid P component by in vitro mutagenesis." From Amyloid & Amyloidosis 1998: Proceedings of the VIIIth International Symposium on Amyloidosis, Rochester, MN, pp. 23-25 (Aug. 7-11, 1998).
Chatziantoniou, et al., "Is Kidney Injury a Reversible Process," Curr. Opin. Nephrology Hypertension, 17(1):76-81 (2008).
Gerhard, et al., "The Status, Quality and Expansion of the NIH Full-Length cDNA Project: The Mammalian Gene Collection (MGC)," Genome Research, 14(10B):2121-2127 (2004).
Giri, S., et al., "Antifibrotic Effect of Decorin in a Bleomycin Hamster Model of Lung Fibrosis," Biochemical Pharmacology, 54:1205-1216 (1997).
Jenny, N. S., et al., "Serum Amyloid P and Cardiovascular Disease in Older Men and Women Results from the Cardiovascular Health Study," Arterioscier. Thromb. Vasc. Biol., 27:352-358 (2007).
Kinoshita CM, et al., "A Protease-Sensitive Site in the Proposed Ca2+-Binding Region of Human Serum Amyloid Component and Other Pentraxins." Protein Sci., 1:700-709 (1992).
Pepys, MB, "Serum Amyloid P. Component. Structure, Function and Role in Amyloidosis." From Amyloid & Amyloidosis 1998: Proceedings of the VIIIth International Symposium on Amyloidosis, Rochester, MN, pp. 6-10 (Aug. 7-11, 1998).
Wang, Q., et al., "Effect of Antibody Against Integrin α4 on Bleomycin-Induced Pulmonary Fibrosis in Mice," Biochemical Pharmacology, 60:1949-1658 (2000).
Yu, L., et al., "Therapeutic Strategies to Halt Renal Fibrosis," Current Opinion in Pharmacology, 2:177-181 (2002).

* cited by examiner

NON-IRRADIATED CONTROL

IRRADIATED + VEHICLE

IRRADIATED + hSAP

```
HOMO SAPIENS     H T D L S G K V F V F P R E S V T D H V N L I T P L E K P L
GALLUS GALLUS    Q E D L Y R K V F V F P R E D P S D A Y V L L Q V Q L E R P L
BOS TAURUS       Q T D L R G K V F V F P P E S T D H V L I T K L E K P L
C. MIGRATORIUS   Q T D L T G K V F V F P R E S E S D Y V K L I P R L E K P L

HOMO SAPIENS     Q N F T L C F R A Y S D L S R A Y S L F S Y N T Q G R D N E
GALLUS GALLUS    L N F T V C L R S Y T D L T R P H S L F S Y A T K A Q D N E
BOS TAURUS       K N L T L C L R A Y S D L S R G Y S L F S Y N I H S K D N E
C. MIGRATORIUS   E N F T L C F R T Y T D L S R P H S L F S Y N T K N K D N E

HOMO SAPIENS     L L V Y K E R V G E Y S L Y I G R H K V T S K V I E K F P A
GALLUS GALLUS    I L F K P K P G E Y R F Y V G G K Y V T F R V P E N R G E
BOS TAURUS       L L V F K N G I G E Y S L Y I G K T K V T V R A T E K F P S
C. MIGRATORIUS   L L I Y K E R M G E Y G L Y I E N V G A I V R G V E E F A S

HOMO SAPIENS     P V H I C V S W E S S G I A E F W I N G T P L V K K G L R
GALLUS GALLUS    W E H V C A S W E S S G I A E F W L N G R P W P R K G L Q
BOS TAURUS       P V H I C T S W E S S G I A E F W I N G K P L V K R G L K
C. MIGRATORIUS   P V H F C T S W E S S G I A D F W V N G I P W V K K G L K
```

Figure 9 (part 1)

| | | | | | | | | | | | | | | | | | | | |
|---|---|---|---|---|---|---|---|---|---|---|---|---|---|---|---|---|---|---|---|
| HOMO SAPIENS | Q | G | Y | F | V | E | A | Q | P | K | I | V | L | G | Q | E | Q | D | S | Y | G | G | K | F | D | R | S | Q | S | F |
| GALLUS GALLUS | K | G | Y | E | V | G | N | E | A | V | V | M | L | G | Q | E | Q | D | A | Y | G | G | F | D | V | Y | N | S | F |
| BOS TAURUS | Q | G | Y | A | V | G | A | H | P | K | I | V | L | G | Q | E | Q | D | S | Y | G | G | F | D | K | N | Q | S | F |
| C. MIGRATORIUS | K | G | Y | T | V | K | T | Q | P | S | I | I | L | G | Q | E | Q | D | N | Y | G | G | F | D | K | S | Q | S | F |

| | | | | | | | | | | | | | | | | | | | |
|---|---|---|---|---|---|---|---|---|---|---|---|---|---|---|---|---|---|---|---|
| HOMO SAPIENS | V | G | E | I | G | D | L | Y | M | W | D | S | V | L | P | P | E | N | I | L | S | A | Y | Q | G | T | P | L | P | A |
| GALLUS GALLUS | T | G | E | M | A | D | V | H | L | W | D | A | G | L | S | P | D | K | M | R | S | A | Y | L | A | L | R | L | P | P |
| BOS TAURUS | M | G | E | I | G | D | L | Y | M | W | D | S | V | L | S | P | E | E | I | L | L | V | Y | Q | G | S | S | I | S |
| C. MIGRATORIUS | V | G | E | M | G | D | L | N | M | W | D | S | V | L | T | P | E | E | I | K | S | V | Y | E | G | S | W | L | E | P |

| | | | | | | | | | | | | | | | | | | | |
|---|---|---|---|---|---|---|---|---|---|---|---|---|---|---|---|---|---|---|---|
| HOMO SAPIENS | N | I | L | D | W | Q | A | L | N | Y | E | I | R | G | Y | V | I | K | P | L | V | W | V | | | | | | | |
| GALLUS GALLUS | A | P | L | A | W | G | R | L | R | Y | E | A | K | G | D | V | V | K | P | R | L | R | E | A | L | G | A | | | |
| BOS TAURUS | P | T | I | L | D | W | Q | A | L | K | Y | E | I | K | G | Y | V | I | V | K | P | M | V | W | G | | | | | |
| C. MIGRATORIUS | N | I | L | D | W | R | A | L | N | Y | E | M | S | G | Y | A | V | I | R | P | R | V | W | H | | | | | | |

Figure 9 (part 2)

METHODS AND COMPOSITIONS USEFUL IN THE TREATMENT OF MUCOSITIS

CROSS-REFERENCE TO RELATED APPLICATION

This application claims the benefit of U.S. application Ser. No. 12/215,700, filed on Jun. 27, 2008, which claims the benefit of U.S. Provisional Application No. 60/958,634, filed on Jul. 6, 2007, the contents of which are incorporated herein by reference in their entirety. This application also claims the benefit of U.S. Provisional Application No. 60/958,634, filed on Jul. 6, 2007, the contents of which are incorporated herein by reference in their entirety. This application also claims the benefit of U.S. Provisional Application No. 60/961,343, filed on Jul. 20, 2007, the contents of which are incorporated herein by reference in their entirety.

BACKGROUND OF THE INVENTION

Mucositis is a condition characterized by swelling, irritation, and discomfort of mucosal linings such as those of the gastrointestinal tract and the oral and oral pharyngeal cavities, and can result in mouth and throat sores, diarrhea, abdominal cramping and tenderness, and rectal ulcerations. This condition occurs in approximately half of all cancer patients undergoing therapy, and is a common side effect of cancer treatments involving radiation and/or chemotherapy. The goal of these approaches to cancer treatment is to kill rapidly dividing cancer cells but, unfortunately, other rapidly dividing cells are killed by the treatment as well, including cells that line regions such as the gastrointestinal tract, leading to mucositis.

The incidence of mucositis, as well as its severity, depends on factors such as the type and duration of the cancer treatment. Mucositis occurs, for example, in virtually all patients who are treated by irradiation of the head and neck. It is also highly prevalent in patients treated with high dose chemotherapy and/or irradiation for the purpose of myeloablation, such as in preparation for stem cell or bone marrow transplantation.

Mucositis adversely impacts the quality of life of cancer patients in several ways. For example, the mouth and throat sores of mucositis can cause significant pain and make it difficult to eat, drink, and even take oral medication. Mucositis is also accompanied by a severe risk of infection, as it can lead to a breach in the otherwise protective linings of the oral mucosa and gastrointestinal tract, which are colonized by a vast array of microorganisms. Gut toxicity is a major limiting factor in radiation and chemotherapy treatment regimes. Further, efforts to counter the discomforts of mucositis can lead to disruptions in cancer treatment, alterations in treatment dosages, or shifting to different modes of treatment. Severe mucositis can also lead to the need for parenteral nutrition or hospitalization. The development of effective approaches to preventing and treating mucositis is therefore important for improving the care of cancer patients.

Alimentary mucositis refers to a form of mucosal barrier injury to the alimentary tract. Alimentary mucositis may occur at a part or multiple parts of the alimentary tract, from mouth to anus, via, e.g., esophagus, stomach, small intestine, colon, and rectum. Non-limiting examples of alimentary mucositis are oral mucositis, esophagitis, stomatitis, enteritis, and proctitis. See, e.g., Blijlevens et al., Bone Marrow Transplant 25:1269-1278 (2000); and Keefe et al., Seminars in Oncology 20:38-47 (2004).

Alimentary mucositis are generally caused by one or more insults, most commonly by a chemical(s) or radiation, or a combination thereof. Radiation may be a result of, e.g., radiation therapy, accidental radiation exposure, and radiation exposure from a terrorist attack. See e.g., Moulder, Int. J. Radiat. Biol. 80:3-10 (2004). Chemical insults are commonly from chemotherapy.

SUMMARY OF THE INVENTION

In part, the disclosure demonstrates that SAP agonists are useful in a treatment for mucositis. One aspect of the invention provides methods for treating, preventing or reducing the severity of mucositis in a patient by administering a therapeutically effective amount of an SAP agonist. The administration of an SAP agonist may delay the development of mucositis, reduce the number of days a patient is afflicted with mucositis, and/or reduce the severity of mucositis.

The application provides methods for treating patients afflicted with mucositis, as well as patients at risk of developing mucositis. Cancer therapy with radiation the, chemotherapy, or a combination thereof are treatments associated with a high risk of mucositis related side effects. The administration of SAP agonists may commence prior, concurrently, or after treatment with radiation therapy or chemotherapy. In some embodiments, patients are afflicted with cancer. In some embodiments, patients are afflicted with lung, ovarian, prostate, lymphoma or gastrointestinal cancer. In some embodiments, patients are afflicted with head and neck cancer or cancer requiring a bone marrow transplant, such as myeloablation therapy.

The application provides methods for treating or preventing a number of related disorders. Methods of the invention are useful for treating oral, esophageal, and gastrointestinal mucositis, as well as gastric and duodenal ulcers, or erosions of the stomach and esophagus.

The application provides SAP agonists useful in the methods of the invention. SAP agonists may increase or mimic SAP signaling or increase SAP activity. A SAP agonist may be a small molecule, nucleic acid, or polypeptide. In exemplary embodiments, the SAP agonist is an SAP polypeptide, an anti-FcγR antibody, laminin, an aggregated IgG antibody, or a cross-linked IgG antibody. In one embodiment, an SAP agonist is provided for use in the treatment of mucositis.

BRIEF DESCRIPTION OF THE DRAWINGS

FIG. 9 depicts the amino acid sequence alignment of human (SEQ ID NO: 1, amino acids 20-223 of Genbank Accession No. NP_001630), *Gallus gallus* (SEQ ID NO: 2, amino acids 20-227 of Genbank Accession No. NP_001034653), *Bos taurus* (SEQ ID NO: 3, amino acids 20-224 of Genbank Accession No. AA102624), and *Cricetulus migratorius* (SEQ ID NO: 4, amino acids 20-223 of Genbank Accession No. AAB28726) serum amyloid P polypeptides (signal sequence not depicted). Amino acids identical to the human SAP are shaded.

DETAILED DESCRIPTION OF THE INVENTION

Overview

Figure 1A:
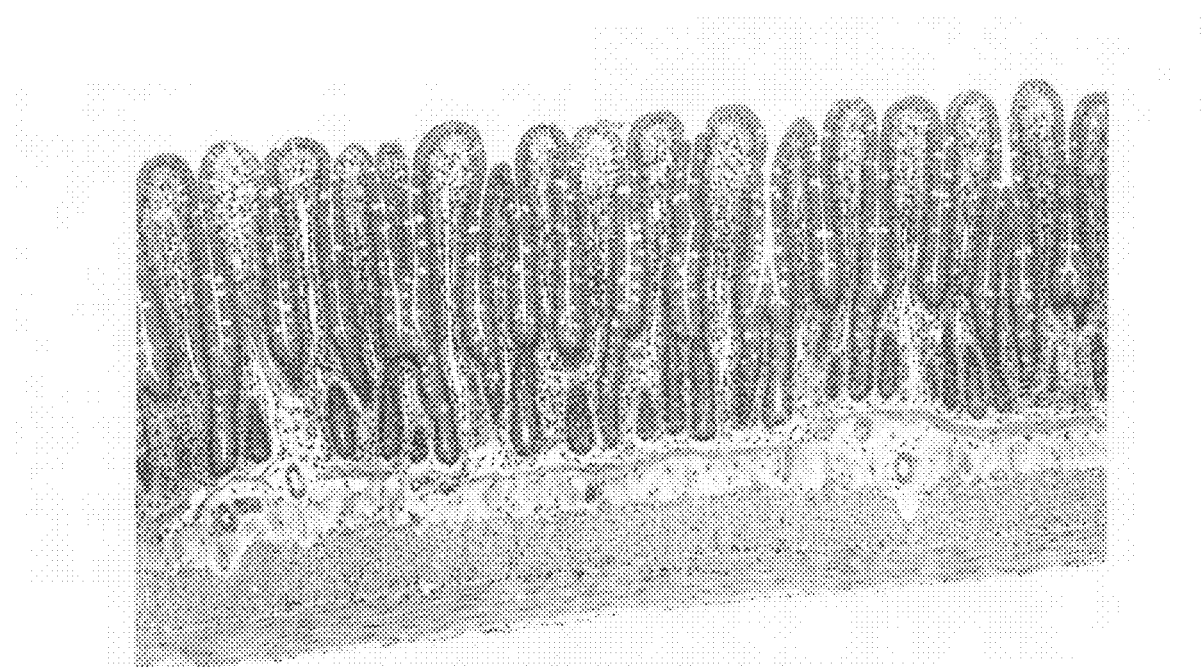
FIG. 1 (A-C) depicts hematoxylin and eosin staining from a rat model of radiation-induced enteropathy. Staining of intestines from non-irradiated control (FIG. 1A), irradiatated vehicle-treated (FIG. 1B) and hSAP-treated rats (FIG. 1C).

One aspect of the present invention relates to the surprising discovery that serum amyloid P (SAP) demonstrates a therapeutic affect in the treatment of mucositis.

Serum amyloid P ("SAP") is a naturally-occurring serum protein in mammals composed of five identical subunits or protomers which are non-covalently associated in a disc-like molecule. SAP is a 125,000 Dalton pentameric glycoprotein composed of five, non-covalently linked, 25,000 Dalton protomers. SAP belongs to the pentraxin superfamily of proteins, characterized by this cyclic pentameric structure. The classical short pentraxins include SAP as well as C-reactive protein. (Osmand, A. P., et al., Proc. Nat. Acad. Sci., 74:739-743 (1977)) It is synthesized in the liver and the physiological half-life of human SAP is 24 hours. The sequence of the human SAP subunit is depicted in SEQ ID NO: 1 (amino acids 20-223 of Genbank Accession No. NP_001630, signal sequence not depicted).

Definitions

As used herein, the terms "treatment", "treating", and the like, refer to obtaining a desired pharmacologic and/or physiologic effect. The effect may be prophylactic in terms of completely or partially preventing a disorder or symptom thereof and/or may be therapeutic in terms of a partial or complete cure for a mucositis disorder and/or adverse affect attributable to the disorder. "Treatment", as used herein, covers any treatment of a disease in a mammal, particularly in a human, and includes: (a) increasing-survival time; (b) decreasing the risk of death due to the disease; (c) preventing the disease from occurring in a subject which may be predisposed to the disease but has not yet been diagnosed as having it; (d) inhibiting the disease, i.e., arresting its development (e.g., reducing the rate of disease progression); and (e) relieving the disease, i.e., causing regression of the disease.

As used herein, a therapeutic that "prevents" a disorder or condition is a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein the terms "subject" and "patient" refer to animals including mammals, in particular humans. The term "mammal" includes primates, domesticated animals including dogs, cats, sheep, cattle, goats, pigs, mice, rats, hamsters, rabbits, guinea pigs, captive animals such as zoo animals, and wild animals. As used herein the term "tissue" refers to an organ or set of specialized cells such as skin tissue, lung tissue, kidney tissue, and other types of cells.

The term "therapeutically effective amount" means an amount of therapeutic agents, or a rate of delivery of such therapeutic agents, effective to facilitate a desired therapeutic effect. The precise desired therapeutic effect will vary according to the mucositis related condition to be treated, the formulation to be administered, and a variety of other factors that are appreciated by those of ordinary skill in the art.

Methods of Treatment

One aspect of the application provides methods for treating, preventing, or reducing the severity of mucositis in a patient, the method comprising administering to a patient in need thereof, a therapeutically effective amount of an SAP agonist.

In some embodiments, administration of an SAP agonist reduces the number of days a patient is afflicted with mucositis. In some embodiments, administration of an SAP agonist delays the development of mucositis. Mucositis that results as a side effect to cancer treatment, generally appears a few days after the start of treatment and can take two to four weeks after cessation of treatment to clear. In some embodiments, administration of an SAP agonist delays the development of mucositis by at least 1, 2, 3, 4, 5, 6, 7, 8, 9, 10, 15, or more days. In some embodiments, administration of an SAP agonist reduces the number of days a patient is afflicted with mucositis by at least 1, 2, 3, 4, 5, 6, 7, 8, 9, 10, 15, or more days. In some embodiments, administration of an SAP agonist speeds the resolution of mucositis.

In some embodiments, administration of an SAP agonist reduces the severity of mucositis by at least one grade according to the National Cancer Institute-Common Toxicity Criteria (NCI-CTC). Various assessment scales exist for the objective classification of mucositis, including the World Health Organization, the Radiation Therapy Oncology Group, the visual analog scale, the oral mucositis scale and the oral mucositis assessment scale, see Sonis, S T, et al. Cancer. 100:1995-2025 (2004) for review. The NCI-CTC provides a grading system from 1-5 for oral mucositis and from 1-4 for gastrointestinal mucositis. A person skilled in the art is capable of assessing the disease progression in a patient to determine the severity of mucositis.

An SAP agonist may be administered to subjects who have recently received or are likely to receive a dose of radiation or toxin. In one embodiment, the dose of radiation or toxin is received as part of a work-related or medical procedure, e.g., working in a nuclear power plant, flying an airplane, an X-ray, CAT scan, or the administration of a radioactive dye for medical imaging; in such an embodiment, the SAP agonist is administered as a prophylactic measure. In another embodiment, the radiation or toxin exposure is received unintentionally, e.g., as a result of an industrial accident, habitation in a location of natural radiation, terrorist act, or act of war involving radioactive or toxic material. In such a case, the SAP agonist is preferably administered as soon as possible after the exposure to inhibit apoptosis and the subsequent development of acute radiation syndrome.

While the methods can be used to treat patients afflicted with mucositis, in some embodiments, the methods are also carried out with patients who do not have, but are at risk of developing mucositis (e.g., cancer or other patients scheduled to receive, currently receiving, or previously treated with radiation and/or chemotherapy). In patients at risk of developing mucositis, treatment according to the invention can reduce the severity of mucositis resulting from their treatment, inhibit the development of mucositis, or prevent the onset of mucositis. In some embodiments, treatment with an SAP agonist delays the onset of symptoms of mucositis by at least 1, 2, 3, 4, 5, 6, 7, 8, 9, 10, 15, or more days. In some embodiments, treatment reduces the number of days a patient is afflicted with mucositis by at least 1, 2, 3, 4, 5, 6, 7, 8, 9, 10, 15, or more days. In some embodiments, treatment reduces the severity of mucositis by at least one grade according to the NCI-CTC grading system.

According to the methods of the invention, an SAP agonist is administered to a patient before, during, and/or after treatment with a therapy that causes mucositis (e.g., oral, alimentary or gastrointestinal mucositis) or puts the patient at risk of developing such mucositis. As is noted above, such treatments include radiation and chemotherapy, which act by blocking the growth of rapidly dividing cells, such as cancer cells and epithelial cells that line the surfaces of the gastrointestinal, respiratory, and genitourinary tracts. Specific examples of treatments that can lead to mucositis include radiation treatment (e.g., head and/or neck, whole body, targeted, and/or hyperfractionated radiation), as well as chemotherapeutic regimens used in the treatment of, or as adjuvant treatments for, conditions such as breast cancer, colon cancer, gastric cancer, genitourinary (e.g., bladder, prostate, or testicular) cancer, gynecologic (e.g., cervical, endometrial, ovarian, or uterine) cancer, head and neck/esophageal cancer, leukemia, lung (small cell or non small-cell) cancer, lymphoma (Hodgkin's or non-Hodgkin's), melanoma, multiple myeloma, pancreatic cancer, and sarcoma. Myeloablative therapy in preparation for bone marrow transplantation can also lead to mucositis.

As is known in the art, cancers such as these can be treated using approaches involving immunotherapy by use of agents such as, for example, rituximab, cetuximab, or bevacizumab, alone or in combination with chemotherapy or radiation therapy. In other examples, chemotherapeutic approaches that may induce mucositis include those utilizing (either as single agents or in combinations) platinum derivatives such as carboplatin, cisplatin, and oxaliplatin; mitosis inhibitors such as paclitaxel, docetaxel, vinorelbine, vincristine, and vinblastine; topoisomerase inhibitors such as etoposide, irinotecan, and topotecan; antimetabolites such as gemcitabine, capecitabine, fludarabine, methotrexate, 5-fluorouracil, cladribine, pentostatin, and cytarabine; DNA synthesis inhibitors such as doxorubicin, epirubicin, idarubicin, daunorubicin, bleomycin, mechlorethamine, and mitoxantrone; alkylating agents such as cyclophosphamide, ifosfamide, and melphalan carmustine; hormonal oncologics such as estramustine; and agents having other or unknown mechanisms such as dacarbazine. Use of these and other approaches to treating cancer is well known to those of skill in the art.

Treatment according to the invention can begin prior to cancer treatment (e.g., 1-2 days or 1 week prior to cancer treatment), at or near the same time as cancer treatment (e.g., simultaneously with, within 1-4 hours of, or on the same day as cancer treatment), or shortly after the cessation of cancer treatment (e.g., within 1-4 days after treatment cessation, and/or prior to or upon appearance of symptoms). Treatment can then be maintained, for example, until any symptoms of mucositis have substantially cleared or the risk of developing such symptoms has passed. Thus, treatment started before or at or near the same time as cancer treatment can be maintained, e.g., for several days. In other examples, treatment is maintained for 1, 2, 3, 4, or more weeks following the cessation of cancer treatment, as determined to be appropriate by one of skill in the art. In specific examples, the treatment according to the present invention is carried out prior to cancer treatment only; prior to and concurrently with cancer treatment only; prior to, concurrently with, and after cessation of cancer treatment; concurrently with cancer treatment only; concurrently with and after cessation of cancer treatment only; after cessation of cancer treatment only; or prior to and after cessation of cancer treatment only. Further, treatment according to the methods of the invention can be altered, stopped, or re-initiated in a patient, depending on the status of any symptoms of mucositis. Treatment can be carried out at intervals determined to be appropriate by those of skill in the art. For example, the administration can be carried out 1, 2, 3, or 4 times or more/day.

The application provides SAP agonists useful for the treatment of mucositis and mucositis related disorders. Mucositis may be oral, gastrointestinal, or esophageal. Disorders that may be treated with SAP agonists include gastric and duodenal ulcers, erosions of the stomach and esophagus, colitis, gastroesophageal reflux, and inflammatory bowel disease. In some embodiments, the inflammatory bowel disease is Crohn's disease or ulcerative colitis.

SAP Agonists

One aspect of the application provides SAP agonists useful in the treatment of mucositis and mucositis related disorders. SAP agonists encompass all compounds and compositions that increase or otherwise mimic endogenous SAP signaling, as well as compounds that increase SAP activity.

(i) Human Serum Amyloid P

In certain embodiments, an SAP signaling agonist is an SAP polypeptide or variant thereof. In certain embodiments, an SAP polypeptide is SAP comprising five human SAP protomers (SEQ ID NO: 1). The term "SAP protomer" is intended to refer to a polypeptide that is at least 60%, at least 70%, at least 80%, at least 85%, at least 90%, at least 95%, at least 97%, at least 99% or 100% identical to human SAP protomer (SEQ ID NO: 1), as determined using the FASTDB computer program based on the algorithm of Brutlag et al. (*Comp. App. Biosci.*, 6:237-245 (1990)). In a specific embodiment, parameters employed to calculate percent identity and similarity of an amino acid alignment comprise: Matrix=PAM 150, k-tuple=2, Mismatch Penalty=1, Joining Penalty=20, Randomization Group Length=0, Cutoff Score=1, Gap Penalty=5 and Gap Size Penalty=0.05. The term "SAP protomer" encompasses functional fragments and fusion proteins comprising any of the preceding. Generally, an SAP protomer will be designed to be soluble in aqueous solutions at biologically relevant temperatures, pH levels and osmolarity. The protomers that non-covalently associate together to form SAP may have identical amino acid sequences and/or post-translational modifications or, alternatively, individual protomers may have different sequences and/or modifications.

Some aspects of the invention provide polypeptides, or provide therapeutic methods for employing those polypeptides, wherein said polypeptides are defined, at least in part, to a reference sequence. Accordingly, such polypeptides may have a certain percentage of amino acid residues which are not identical to a reference sequence. In some embodiments, the non-identical residues have similar chemical properties to the residues to which they are not identical. Groups that have similar properties include the following amino acids: E, D, N, Q; H, K, R; Y, F and W; I, L, V, M, C, A; and S, T, C, P, A.

In some embodiments, the residues that are not identical are those which are not evolutionarily conserved between the reference sequence and an orthologous sequence in at least one evolutionarily related species, such as in species within the same order. In the case of a vertebrate reference sequence, the amino acids that may be mutated in a preferred embodiment are those that are not conserved between the reference sequence and the orthologous sequence in another vertebrate species. For example, if a polypeptide used in a method of the present invention is said to comprise an amino acid sequence that is at least 95% identical to human SAP (SEQ ID NO:1), then said polypeptide may have non-identical residues to those positions in which the human SAP and that of another vertebrate differ. FIG. 9 depicts human SAP aligned against two mammalian and one avian SAP sequence. Unshaded residues indicate residues that differ from the human SAP sequence.

Polypeptides sharing at least 95% identity with SEQ ID NO:1 include polypeptides having conservative substitutions in these areas of divergence. Typically seen as conservative substitutions are the replacements, one for another, among the aliphatic amino acids Ala, Val, Leu, and Ile, interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Additional guidance concerning which amino acid changes are likely to be phenotypically silent can be found in Bowie et al., Science 247:1306-1310 (1990).

In certain embodiments, SAP polypeptides comprising polymers that are at least 60%, at least 70%, at least 80%, at least 85%, at least 90%, at least 95%, at least 97%, or at least 99% identical to SEQ ID NO. 1 increase SAP signaling.

In certain embodiments, an SAP signaling agonist is an SAP variant. The term "SAP variant" is intended to refer to a protein comprising from two to five SAP protomers that demonstrates one or more of the following features as compared to the human SAP pentamer: increased plasma half-life, increased in vitro stability, or increased in vivo stability relative to human SAP.

In specific embodiments of the present invention, compositions containing SAP, SAP variants, or SAP functional fragments may be operable to raise SAP concentration in target locations to approximately at least 0.5 µg/ml. In humans, $I^{125}$ radiolabelled SAP has been previously administered to study patients with amyloidosis. In the treatments, approximately 600 µg of SAP was administered to an adult human. Accordingly, administration of approximately 600 µg of SAP systemically to an adult human is safe. Higher dosages may also be safe under appropriate conditions.

(ii) Anti-FcγR Antibodies

In one aspect of the invention, one or more compounds are provided that mimic SAP signaling. In some embodiments, the SAP signaling agonists are anti-FcγR antibodies. Anti-FcγR antibodies are IgG antibodies that bind to receptors for the Fc portion of IgG antibodies (FcγR). The anti-FcγR antibodies bind through their variable region, and not through their constant (Fc) region. The anti-FcγR antibodies may be further cross-linked or aggregated.

FcγR are found on the surface of a variety of hematopoietic cells. There are four distinct classes of FcγR. FcγRI (CD64) is expressed by peripheral blood monocytes and binds monomeric IgG with a high affinity. FcγRII (CD32) and FcγRIII (CD16) are low affinity receptors for IgG and only efficiently bind aggregated IgG. FcγRII is expressed by peripheral blood B cells and monocytes, whereas FcγRIII is expressed by NK cells and a subpopulation of monocytes. FcγRIV was recently identified in mice and is present on murine peripheral blood monocytes and neutrophils, macrophages and dendritic cells and efficiently binds murine IgG2a and IgG2b antibodies. There is a putative human FcγRIV gene, but the biological function of the protein, such as ligand specificity and cellular expression is, as yet unknown.

Peripheral blood monocytes express both FcγRI and FcγRII (a subpopulation, of monocytes express FcγRIII), whereas tissue macrophages express all three classical FcγR. Clustering of FcγR on monocytes by IgG, either bound to pathogens or as part of an immune complex, initiates a wide variety of biochemical events.

Anti-FcγR antibodies for FcγRI (anti-FcγRI), for FcγRII (anti-FcγRII) and FcγRIII are able to bind to either FcγRI, FcγRII, or FCγIII respectively. These FcγR may then be cross-linked by the binding of additional antibodies or other means. This process initiates intracellular signaling events consistent with FcγR activation.

In specific embodiments, compositions containing approximately 1 µg/ml anti-FcγR antibodies may be effective to treat, inhibit or reduce the severity of mucositis. In other embodiments, compositions may contain an amount sufficient to deliver 1 µg/ml anti-FcγR antibodies to the target tissue.

Anti-FcγR antibodies may be administered in a dose of approximately 1.0 µg/mL, in an amount sufficient to deliver 1 µg/ml anti-FcγR antibodies to the target tissue, or in another dose sufficient to treat mucositis without causing an undesirable amount of cell death in the patient.

Anti-FcγR antibodies used in examples of the present disclosure include anti-FcγRI antibodies and anti-FcγRII antibodies. The anti-FcγRI antibodies, anti-FcγRII antibodies, and anti-FcγRIII may be further cross-linked or aggregated.

Anti-FcγR antibodies may include any isotype of antibody.

(iii) Aggregated Fc Domains and Fc-containing Antibodies

In some embodiments, the SAP signaling agonists are cross-linked or aggregated IgG. IgG from the appropriate source (e.g. human IgG for human receptors) may normally bind to FcγR through its Fc region. Cross-linked or aggregated IgG may include any IgG able to bind the target FcγR through its Fc region, provided that at least two such IgG antibodies are physically connected to one another.

Antibodies of both types may include whole antibodies or a portion thereof. For example, they may include any antibody portion able to cross-link FcγR. This may include aggregated or cross-linked antibodies or fragments thereof, such as aggregated or cross-linked whole antibodies, $F(ab')_2$ fragments, and possible even Fc fragments.

Aggregation or cross-linking of antibodies may be accomplished by any known method, such as heat or chemical aggregation. Antibodies may be polyclonal or monoclonal, such as antibodies produced from hybridoma cells. Compositions and methods may employ mixtures of antibodies, such as mixtures of multiple monoclonal antibodies, which may be cross-linked or aggregated to like or different antibodies.

Compositions containing cross-linked or aggregated IgG may treat, prevent or reduce the severity of mucositis in a patient.

In other specific embodiments, compositions may contain as little as 0.1 µg ml cross-linked or aggregated IgG. Aggregated or cross-linked IgG may be administered in an amount sufficient to deliver at least 0.1 µg/ml IgG to the target tissue, or in another dose sufficient to treat, prevent or reduce the severity of mucositis in the patient.

(iv) Increase SAP Activity

In some embodiments, an SAP agonist increases SAP activity. SAP activity can be increased by increasing the concentration of SAP by, for example, increasing SAP transcription, increasing translation, increasing SAP secretion, increasing SAP RNA stability, increasing SAP protein stability, or decreasing SAP protein degradation. SAP activity can also be increased by increasing specifically the "free concentration" of SAP or rather the unbound form by, for example, decreasing SAP endogenous binding partners.

In some embodiments, an SAP agonist is an aptamer. Aptamers, are oligonucleotides, which can be synthetic or natural, that bind to a particular target molecule, such as a protein or metabolite. Typically, the binding is through interactions other than classic Watson-Crick base pairing.

Aptamers represent a promising class of therapeutic agents currently in pre-clinical and clinical development. Like biologics, e.g., peptides or monoclonal antibodies, aptamers are capable of binding specifically to molecular targets and, through binding, inhibiting target function. A typical aptamer is 10-15 kDa in size (i.e., 30-45 nucleotides), binds its target with sub-nanomolar affinity, and discriminates among closely related targets (e.g., will typically not bind other proteins from the same gene family) (Griffin, et al. (1993), Gene 137(1): 25-31; Jenison, et al. (1998), Antisense Nucleic Acid Drug Dev. 8(4): 265-79; Bell, et al. (1999), In Vitro Cell. Dev. Biol. Anim. 35(9): 533-42; Watson, et al. (2000), Antisense Nucleic Acid Drug Dev. 10(2): 63-75; Daniels, et al. (2002), Anal. Biochem. 305(2): 214-26; Chen, et al. (2003), Proc. Natl. Acad. Sci. U.S.A. 100(16): 9226-31; Khati, et al. (2003), J. Virol. 77(23): 12692-8; Vaish, et al. (2003), Biochemistry 42(29): 8842-51).

Aptamers can be created by an entirely in vitro selection process (Systematic Evaluation of Ligands by Experimental Enrichment, i.e., SELEX™) from libraries of random sequence oligonucleotides as described in U.S. Pat. Nos. 5,475,096 and 5,270,163. Aptamers have been generated against numerous proteins of therapeutic interest, including growth factors, enzymes, immunoglobulins, and receptors (Ellington and Szostak (1990), Nature 346(6287): 818-22; Tuerk and Gold (1990), Science 249(4968): 505-510).

Aptamers have a number of attractive characteristics for use as therapeutics. In addition to high target affinity and specificity, aptamers have shown little or no toxicity or immunogenicity in standard assays (Wlotzka, et al. (2002), Proc. Natl. Acad. Sci. U.S.A. 99(13): 8898-902). Indeed, several therapeutic aptamers have been optimized and advanced through varying stages of pre-clinical development, including pharmacokinetic analysis, characterization of biological efficacy in cellular and animal disease models, and preliminary safety pharmacology assessment (Reyderman and Stavchansky (1998), Pharmaceutical Research 15(6): 904-10; Tucker et al., (1999), J. Chromatography B. 732: 203-212; Watson, et al. (2000), Antisense Nucleic Acid Drug Dev. 10(2): 63-75).

A suitable method for generating an aptamer to a target of interest is with the process entitled "Systematic Evolution of Ligands by EXponential Enrichment" ("SELEX™"). The SELEX™ process is a method for the in vitro evolution of nucleic acid molecules with highly specific binding to target molecules and is described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands". Each SELEX™-identified nucleic acid ligand is a specific ligand of a given target compound or molecule. The SELEX™ process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets. The SELEX™ method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX™ method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule. Systematic Evolution of Ligands by Exponential Enrichment, "SELEX™," is a method for making a nucleic acid ligand for any desired target, as described, e.g., in U.S. Pat. Nos. 5,475,096 and 5,270,163, and PCT/US91/04078, each of which is specifically incorporated herein by reference.

In some embodiments, the aptamer is an agonist-aptamer, i.e., activates the activity of a target when it binds thereto. An agonist-aptamer may bind and activate, for example, FcγRI or FcγRII. In some embodiments, the aptamer is an antagonist-aptamer, i.e., inactivates/inhibits the activity of a target when it binds thereto. An antagonist-aptamer may bind and inhibit, for example, an SAP inhibitor.

Fc-Receptors

Receptors for immunoglobulins (Fc-receptors or FcRs) are widely expressed throughout the immune system. By binding to the antibody Fc-portion, they provide a link between the specificity of the adaptive immune system and the effector functions triggered by innate immune effector cells. Co-expression of activating and inhibitory FcRs on the same cell establishes a threshold for immune cell activation by immune complexes (combination of an epitope with an antibody directed against that epitope). Besides their involvement in the efferent phase of an immune response, they are also important for modulating adaptive immune responses by regulating B cell and dendritic cell (DC) activation. Uptake of immune complexes by FcRs on DCs and the concomitant triggering of activating and inhibitory signaling pathways will determine the strength of the initiated T-cell response. Loss of this balanced signaling results in uncontrolled responses that can lead to the damage of healthy tissues and ultimately to the initiation of autoimmune processes.

FcRs are widely expressed on cells of the immune system and select other cell types, such as endothelial cells, mesangial cells, and osteoclasts; one of the few hematopoietic cell types that do not show notable FcR expression are T cells. Four different classes of FcRs have been identified in rodents: FcγRI, FcγRIIB, FcγRIII, and FcγRIV. FcγRs are well conserved between different mammals and orthologous proteins to these rodent receptors were found in most species. The corresponding human proteins are called FcγRIA, FcγRIIB (CD32B), FcγRIIA (CD32A), FcγRIIC, FcγRIIIA (CD16), and FcγRIIIB. Although the extracellular portion of FcγRIIA is highly homologous to mouse FcγRIII, the intracellular portion differs significantly. Other human FcR genes such as FcγRIB and FcγRIC do not code for functional proteins due to disrupted open reading frames. In addition, FcγRIIIB, a GPI-anchored FcR selectively expressed on neutrophils, is not found in mice.

On a functional level, FcRs can be classified in two ways: first, based on the affinity for their ligand and second, based on the type of signaling pathway that is initiated on FcR cross-linking. The majority of FcRs including FcγRIIB, FcγRIII, and FcγRIV as well as their corresponding human counterparts FcγRIIA/B/C and FcγRIIIA/B have a low affinity for the IgG Fc-portion in the micromolar range ($10^{-5}$ to $10^{-7}$). Only FcγRI displays a higher affinity ($10^8$-$10^9$ M$^{-1}$) enabling significant binding to monomeric antibodies. All other FcRs selectively interact with antibodies in the form of immune complexes, which usually consist of multiple antibodies bound to their target antigen. FcRs differ in regard to the signaling pathways they initiate. The activating receptors (FcγRI, FcγRIIA and FcγRIIIA) contain an Immunoreceptor Tyrosine-based Activation Motif (ITAM) in their cytoplasmic region or in their associated signal transduction region. They stimulate immune effector cell activation/proliferation, release of inflammatory mediators, oxidative burst, phagocytosis and antigen presentation. The inhibitory receptors (FcγRIIB1 and FcγRIIB2) contain an Immunreceptor Tyrosine-based inhibitory Motif (ITIM) in their cytoplasmic tail. In cells expressing both receptor classes, the immune response depends on the ratio between activating and inhibiting receptors, and hence on the cytokine environment. Th1 and Th2 cytokines up-regulate the expression of activating and inhibitory receptors respectively.

All of these "activating" FcRs contain ITAM in their cytosolic portion that become tyrosine-phosphorylated by members of the Src family of kinases. Phosphorylation of the ITAM sequences creates SH2 sites for docking and activation of Syk kinases. Depending on the cell type and individual FcR, the involved Src kinase family members might vary. For example, Lyn is associated with the FcγRI pathway in mast cells, whereas Lck is associated with FcγRIIIA in NK cells. In macrophages both of these kinases, as well as Hck, are associated with FcγRI and FcγRIIA (Takai, 2002). Following the phosphorylation of the ITAM motif, the recruitment and activation of Syk kinases ensues that leads to the recruitment of a variety of intracellular substrates, including PI3K, Btk and other Tec family kinases, phospholipase C-γ (PLCγ), and adaptor proteins such as SLP-76 and BLNK. Moreover, the Ras/Raf/MAP kinase pathway is activated through Sos bound to Grb2 that is recruited on phosphorylation of Shc. Another crucial step is the activation of PI3K by Syk, which results in the generation of phosphatidyl-inositol-3-phosphates. This leads to the recruitment of Btk and PLCγ that recognize PIP3 with their pleckstrin homology (PH) domains leading to the production of inositol triphosphate (IP3) and diacylglycerol (DAG), which are crucial for the mobilization of intracellular calcium and activation of protein kinase C (PKC). This signaling cascade initiates inflammatory, cytolytic and phagocytic activities of immune effector cells.

The role of the inhibitory receptor signaling is to dampen these activating pathways by interfering with the generation of key intermediates such as PIP3. This is initiated by phosphorylation of the ITIM motif in the cytosolic portion of FcγRIIB by Lyn that leads to the recruitment and activation of the SH2-domain containing inositol phosphatase (SHIP). The key function of activated SHIP is to hydrolyze phosphatidyl inositol intermediates, such as PIP3, and thereby to interfere with the membrane recruitment of Btk and PLCγ, thus dampening ITAM signaling mediated calcium release and downstream effector functions such as ADCC, phagocytosis, cytokine secretion, and release of inflammatory mediators. The Ras pathway is also inhibited by recruitment of Shc and DOK to tyrosine-phosphorylated SHIP, which inhibits cell proliferation.

Pharmaceutical Preparations and Formulations

In certain embodiments, the methods described herein involve administration of an SAP agonist to a subject. The SAP agonists may be formulated in a conventional manner using one or more physiologically acceptable carriers or excipients. For example, SAP agonists may be formulated for administration by, for example, injection (e.g. SubQ, IM, IP), inhalation or insufflation (either through the mouth or the nose) or oral, buccal, sublingual, transdermal, nasal, parenteral or rectal administration. In certain embodiments, SAP agonists may be administered locally, at the site where the target cells are present, i.e., in a specific tissue, organ, or fluid (e.g., blood, cerebrospinal fluid, tumor mass, etc.).

SAP agonists can be formulated for a variety of modes of administration, including systemic and topical or localized administration. Techniques and formulations generally may be found in Remington's Pharmaceutical Sciences, Meade Publishing Co., Easton, Pa. For parenteral administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets, lozanges, or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation (e.g., pulmonary delivery), SAP agonists may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin, for use in an inhaler or insufflator may be formulated containing a powder mix of the compound and a suitable powder base such as lactose or starch.

SAP agonists may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In addition, SAP agonists may also be formulated as a depot preparation. Such long acting formulations may be administered by implantation (for example subcutaneously or intramuscularly) or by intramuscular injection. Thus, for example, SAP agonists may be formulated with suitable polymeric or hydrophobic materials (for example as an emulsion in an acceptable oil) or ion exchange resins, or as sparingly soluble derivatives, for example, as a sparingly soluble salt. Controlled release formula also includes patches.

In certain embodiments, SAP agonists are incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Pharmaceutical compositions may comprise from about 0.00001 to 100% such as from 0.001 to 10% or from 0.1% to 5% by weight of one or more SAP agonists described herein. In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

An example of formulation for human SAP (hSAP) would be 0.5-15 mg/mL hSAP dissolved in water for injection containing 1-20 mM Tris, 140 mM NaCl with buffer to a pH of 7.0-9.0. A more preferred example of formulation for human SAP (hSAP) would be 5 mg/mL hSAP dissolved in water for injection containing 10 mM Tris, 140 mM NaCl with phosphate buffer to a pH of 8.0.

SAP agonists described herein may be stored in oxygen free environment according to methods in the art.

Combination Treatment

The methods of the invention can be used alone or in conjunction with other approaches for reducing the severity of mucositis. For example, the methods of the invention can be carried out in combination with antimicrobial or antifungal therapies, e.g., therapies involving administration of antibiotics such as nystatin, amphotericin, acyclovir, valacyclovir, clotimazole, fluconazole, and tetracycline compounds (include doxycycline, minocycline, tetracycline, oxytetracycline, chlortetracycline, demeclocycline, lymecycline, and sancycline). As a specific example of such treatment, patients with head and neck cancer receiving radiotherapy have colonization of the oropharyngeal region with gram-negative bacteria. Selective decontamination of the oral cavity with antimicrobial agents has the benefit of reducing oral mucositis associated with radiation therapy, but there may be limitations to the beneficial effects of such treatment. Anti-microbial therapy can kill bacteria, but cannot reduce endotoxin, and indeed may actually increase endotoxin. As endotoxin is a potent mediator of inflammation, it may contribute to the aggravation of mucositis and, thus, co-treatment with an anti-endotoxin compound (e.g., a Lipid A analog, such as eritoran) and antibiotics can be used as a more effective approach to treating oral mucositis in such patients, according to the invention.

Antibiotic lozenges designed to dissolve in the mouth and decontaminate the oral mucosa have been developed and have been widely recommended to reduce oral infections associated with mucositis. The lozenges may contain polymixin E, tobramycin and amphotericin B, which together provide broad spectrum antibacterial and antifungal cover. These are commonly known as PTA lozenges or PTA pastilles. There is evidence supporting the use of PTA lozenges in preventing infectious complications of mucositis in cancer patients undergoing radiotherapy.

Some anti-viral therapies have been developed to treat patients suffering from mucositis that have an underlying viral infection. Acyclovir is an antiviral agent which is active against the Herpes species that commonly infect the oral mucous membranes in immunosuppressed cancer patients.

IL-11 has been investigated to mitigate the mucotoxic effects of radiation therapy and chemotherapy and have demonstrated activity in small animal trials. According to the present invention, IL-11, analogs, and derivatives thereof, are administered to patients conjointly with SAP agonists, either prophylactically or at the onset of symptoms associated with the aforementioned disorders. IL-11 and SAP agonists can be administered in suitable pharmaceutically acceptable carriers either alone or in combination with other conventional agents useful in alleviating the symptoms associated with the aforementioned disorders.

In one embodiment, the present invention comprises preparations of IL-11 and SAP agonists that are suitable for oral delivery to the mouth. Suitable oral preparations may be prepared with aqueous-based solutions such as sodium bicarbonate (e.g., Brioschi®), or in gels and suspensions for topical administration in the mouth. Oral preparations may also take the form of patches for delivery of IL-11 and SAP agonists to the mouth via sustained release. Additional oral preparations may comprise IL-11 and SAP agonists in the form of a lozenge or an uncoated tablet which is retained in the mouth. The oral preparations are particularly well-suited for disorders and inflammatory responses involving the mucosa of the head, neck and/or mouth. Such conditions include oral mucositis. Such conditions may result, for example, from chemotherapy or radiotherapy for head and neck cancer, cervical esophageal cancer or lung cancer.

In other embodiments, the present invention comprises preparations of IL-11 and SAP agonists which are suitable for topical delivery for mucosa and/or dermis. Such topical preparations may be prepared in the form of aqueous-based solutions, gels, ointments or creams for topical administration, as gels and suspensions for cervical administration, as pills, tablets, capsules or suppositories for immediate or sustained release to the gastrointestinal tract, or in the form of solution for enema. Such topical preparations are especially suited for treatment of disorders relating to local regions, such gastrointestinal mucositis. Some of these conditions may result, for example, from chemotherapy and/or radiotherapy for colorectal cancer, prostate cancer, cervical esophageal cancer or lung cancer. Among the reasons that local administration may be preferred are the ease of administering a topical formulation compared to administration of subcutaneous injectable formulations. In certain classes of patients, the toxicity profile of chemotherapeutic agents may be such that concurrent parenteral administration of IL-11 is relatively unsuited. Other patients may have medical conditions for which the adverse event profile of parenteral IL-11 is relatively unsuited.

Suitable doses of IL-11 agonists may be administered from once a week up to about six times daily. Treatment may continue for a period of between one day and six months, or for as long as is deemed necessary and safe in the treatment of the aforementioned disorders, as is readily ascertained by standard tests by the attending physician, depending upon the nature of the disorder being treated.

The methods of the invention can also be used in conjunction with palliative therapies including the use of topical rinses, gels, or ointments that include lidocaine, articaine, and/or morphine, as well as other analgesic or anti-inflammatory agents. Specific examples of other agents and approaches that can be used in combination with SAP agonists, according to the methods of the invention, include the following: velafermin (CG53135/fibroblast growth factor-20/FGF-20, CuraGen), palifermin (recombinant keratinocyte growth factor; rHuKGF; Kepivance™; Amgen) and AES-14 (uptake-enhanced L-glutamine suspension) (Peterson, J. Support Oncol. 4(2 Suppl. 1)9-13, 2006); oral cryotherapy (including beta-carotene, vitamin E, oxpentifylline, azelastine hydrochloride, and prostaglandins E1 and E2), low-level laser therapy, chlorhexidine, amifostine, hematologic growth factors, pentoxifylline, and glutamine (Saadeh, Pharmacotherapy 25(4):540-554, 2005); amifostine, antibiotic paste or pastille, hydrolytic enzymes, ice chips, benzydamine, calcium phosphate, honey, oral care protocols, povidone, and zinc sulphate (Worthington et al., Cochrane Database Syst. Rev. 2:CD000978, 2006); flurbiprofen (e.g., administered as a tooth patch; Stokman et al., Support Care Cancer 13(1):42-48, 2005); diphenhydramine, magnesium hydroxide/aluminum hydroxide, nystatin, and corticosteroids (Chan et al., J. Oncol. Pharm. Pract. 11 (4): 139-143, 2005) including prednisone (for short term systemic therapy), flucinonide and globetasol (for topical therapy), and elixir dexamthasone (for oral therapy); oral transmucosal fentanyl citrate (e.g., administered in the form of a lozenge; Shaiova et al., Support Care Cancer 12(4):268-273, 2004); clonazepam (e.g., in the form of a tablet; Gremeau-Richard et al., Pain 108(102):51-57, 2004); capsaicin (e.g., in the form of a lozenge; Okuno et al., J. Cancer Integr. Med. 2(3):179-183, 2004); ketamine (e.g., in the form of an oral rinse; Slatkin et al., Pain Med. 4(3):298-303, 2003); and granulocyte-macrophage colony-stimulating factor (GM-CSF)/granulocyte colony-stimulating factor (G-CSF), Transforming Growth Factor-B 3 (TGF-B 3), keratinocyte growth factor 1, laser light therapy, N-acetylcyteine (NAC, Lappas, 2003. J. Clin Endocrinoloyg Metab) and glutamine supplements (Duncan et al., Aliment. Pharmacol. Ther. 18(9):853-874, 2003); mucosal barrier and coating agents (including sueralfate, sodium alginante, kaolin-pectin, plastic wrap film, radiation guards, and antacids); chamomile; allouprinol; propantheline; silver nitrate COX-1 or COX-2 antagonist (including indomethacin and flurbriprofin); IL-6 antagonist, a TNF-α antagonist; L-1 antagonist, interferon-gamma antagonist; NO antagonist (aminoguanidine and guanidine); mast cell antagonist (antihistamines, serine protease inhibitors, or degranulation inhibitors); aminophosphorothioate or aminoalkyl thiol compounds; resveratrol; NF-κB antagonist; angiotensinogen, angiotensin I (AI), AI analogues, AI fragments and analogues thereof, angiotensin II (AII), AII analogues, AII fragments or analogues thereof, or AII AT.sub.2 type 2 receptor agonists; bismuth-containing compound (bismuth salt or bismuth complex)

In certain embodiments, the methods described herein involve administration of an anti-mucositis therapeutic and a SAP agonist. These therapeutic agents may be formulated to be administered conjointly using one or more physiologically acceptable carriers. These combinational therapeutics can be formulated for a variety of modes of administration, including systemic and topical or localized administration as described herein for the administration of SAP and SAP agonists.

In certain embodiments, the anti-mucositis therapeutic may be formulated for sustained release of the SAP and/or and additional anti-mucositis therapeutic. Formulations for sustained release may be administered using one or more physiologically acceptable carriers. These combinational therapeutics can be formulated for a variety of modes of administration, including systemic and topical or localized administration as described herein for the administration of SAP and SAP agonists. In certain embodiments, the anti-mucositis therapeutic may be administer to a patient to prevent or reduce the severity of oral mucositis.

The present invention provides anti-mucositis therapeutic comprising an orally acceptable carrier. As used herein, an "orally acceptable carrier" refers to a material or combination of materials that are safe for use in the compositions of the present invention, commensurate with a reasonable benefit/risk ratio, with which the anti-mucositis therapeutic may be associated while retaining significant efficacy. Preferably, the carrier does not substantially reduce the efficacy of the anti-mucositis therapeutic. Selection of specific carrier components is dependant on the desired product form, including dentifrices, rinses, gels, and paints. In various embodiments, the carrier is operable to sufficiently adhere the anti-mucositis therapeutic against surfaces within the oral cavity to which the composition is administered, without concomitant use of a dental tray, mouthpiece, tape, or similar appliance. In various embodiments, the carrier is operable for use with a tape, tray, mouthpiece or similar appliance. In some embodiments, the anti-mucositis therapeutic includes SAP agonists in an orally acceptable formulation. In some embodiments, the anti-mucositis therapeutic includes SAP agonist and additional active agents in an orally acceptable formulation.

Materials among those that are useful in carriers include adhesion agents, viscosity modifiers, diluents, surfactants, foam modulators, peroxide activators, peroxide stability agents, abrasives, pH modifying agents, humectants, mouth feel agents, sweeteners, flavorants, colorants, and combinations thereof. It is understood that while general attributes of each of the above categories of materials may differ, there may be some common attributes and any given material may serve multiple purposes within two or more of such categories of materials. Preferably, such carrier materials are selected for compatibility with the anti-mucositis therapeutic agent and with other ingredients of the composition.

In some embodiments, concurrent administration of an SAP agonist and an additional agent, such as velafermin, palifermin, or an antimicrobial or antifungal agent, reduces the effective therapeutic dosage of the SAP agonist and/or the additional agent as compared to the dosage required for a therapeutic effect when administered alone. In some embodiments, the concurrent administration further reduces the number of days a patient is afflicted with mucositis as compared to administration with an SAP agonist or the additional agent alone. In some embodiments, the concurrent administration further delays the development of mucositis in a patient as compared to administration with an SAP agonist or the additional agent alone. In some embodiments, the concurrent administration further reduces the severity of mucositis in a patient as compared to administration with an SAP agonist or the additional agent alone.

SEQUENCE LISTING

SEQ ID NO: 1
human serum amyloid protein P
HTDLSGKVFVFPRESVTDHVNLITPLEKPLQNFTLCFRAYSDLSRAYSLF

SYNTQGRDNELLVYKERVGEYSLYIGRHKVTSKVIEKFPAPVHICVSWES

-continued

SSGIAEFWINGTPLVKKGLRQGYFVEAQPKIVLGQEQDSYGGKFDRSQSF

VGEIGDLYMWDSVLPPENILSAYQGTPLPANILDWQALNYEIRGYVIIKP

LVWV

SEQ ID NO: 2
Gallus gallus serum amyloid protein P
QEDLYRKVFVFREDPSDAYVLLQVQLERPLLNFTVCLRSYTDLTRPHSLF

SYATKAQDNEILLFKPKPGEYRFYVGGKYVTFRVPENRGEWEHVCASWES

GSGIAEFWLNGRPWPRKGLQKGYEVGNEAVVMLGQEQDAYGGGFDVYNSF

TGEMADVHLWDAGLSPDKMRSAYLALRLPPAPLAWGRLRYEAKGDVVVKP

RLREALGA

SEQ ID NO: 3
Bos taurus serum amyloid protein P
QTDLRGKVFVFPRESSTDHVTLITKLEKPLKNLTLCLRAYSDLSRGYSLF

SYNIHSKDNELLVFKNGIGEYSLYIGKTKVTVRATEKFPSPVHICTSWES

STGIAEFWINGKPLVKRGLKQGYAVGAHPKIVLGQEQDSYGGGFDKNQSF

MGEIGDLYMWDSVLSPEEILLVYQGSSSISPTILDWQALKYEIKGYVIVK

PMVWG

SEQ ID NO: 4
Cricetulus migratorius serum amyloid protein P
QTDLTGKVFVFPRESESDYVKLIPRLEKPLENFTLCFRTYTDLSRPHSLF

SYNTKNKDNELLIYKERMGEYGLYIENVGAIVRGVEEFASPVHFCTSWES

SSGIADFWVNGIPWVKKGLKKGYTVKTQPSIILGQEQDNYGGGFDKSQSF

VGEMGDLNMWDSVLTPEEIKSVYEGSWLEPNILDWRALNYEMSGYAVIRP

RVWH

EXEMPLIFICATION

Example 1

Human SAP (hSAP) was evaluated in a unique rat model of radiation-induced enteropathy (Hauer-Jensen, 1988). Briefly, a bilateral orchiectomy was performed on male rats and a loop of the small intestine was sutured to the inside of the scrotum, producing an artificial hernia. On study day 0, a single 17 Gy dose of localized irradiation was delivered to the short segment of small intestine located inside the scrotum, while the remainder of the intestine was shielded from damage. Rats were dosed i.p. with 480 µg of hSAP (n=15) or vehicle (n=17) immediately following irradiation; subsequent doses were administered on Days 2, 4, 6, 8, 10 and 12. Rats were sacrificed on day 14, and sections of irradiated and shielded intestine were processed for histologic evaluation. A histopathologic radiation injury score (RIS) (Hauer-Jensen, 1983) comprising 7 parameters of early (2 weeks) and late developing (12 wk-26 wk) enteropathy was used to quantify radiation injury. Quantitative immunohistochemistry, total collagen content and RT-PCR were also conducted.

Figure 1B:
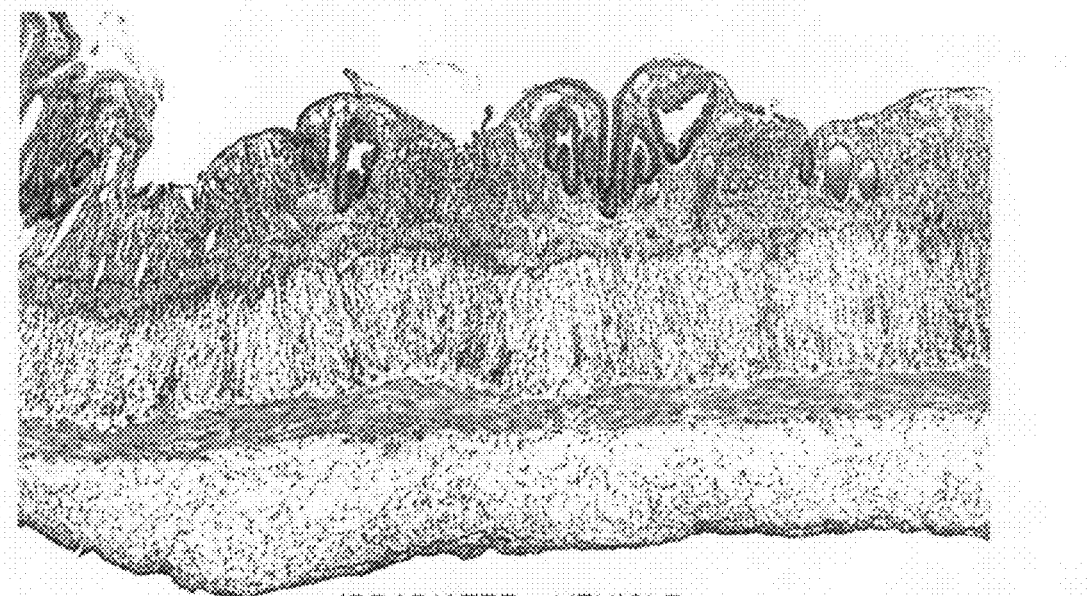
Figure 1C:
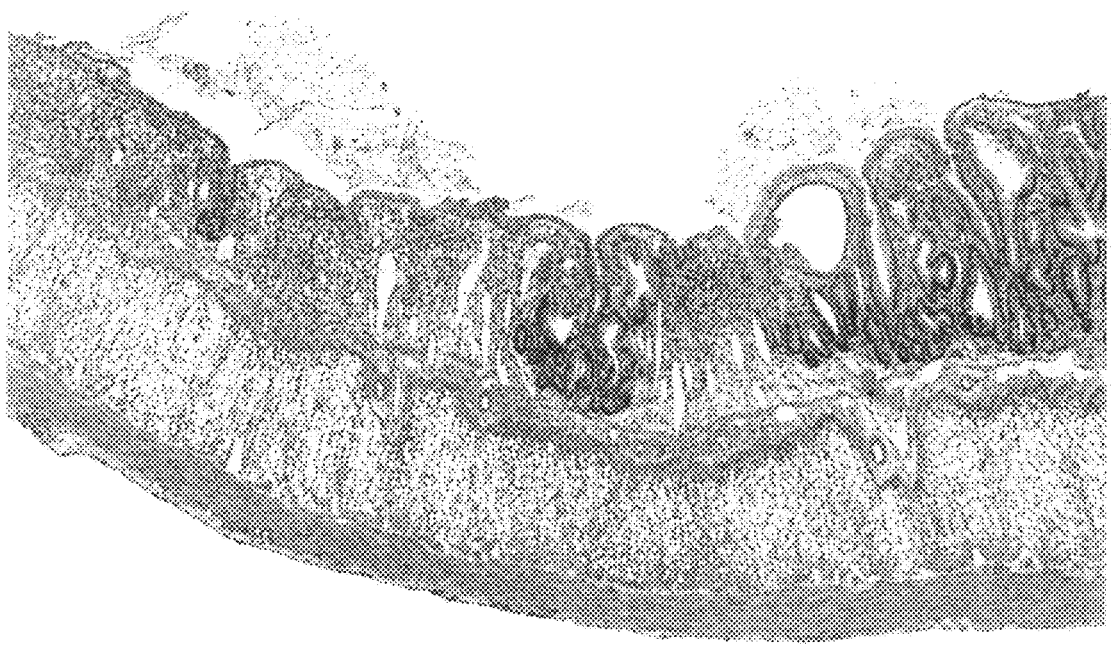
Figure 2:
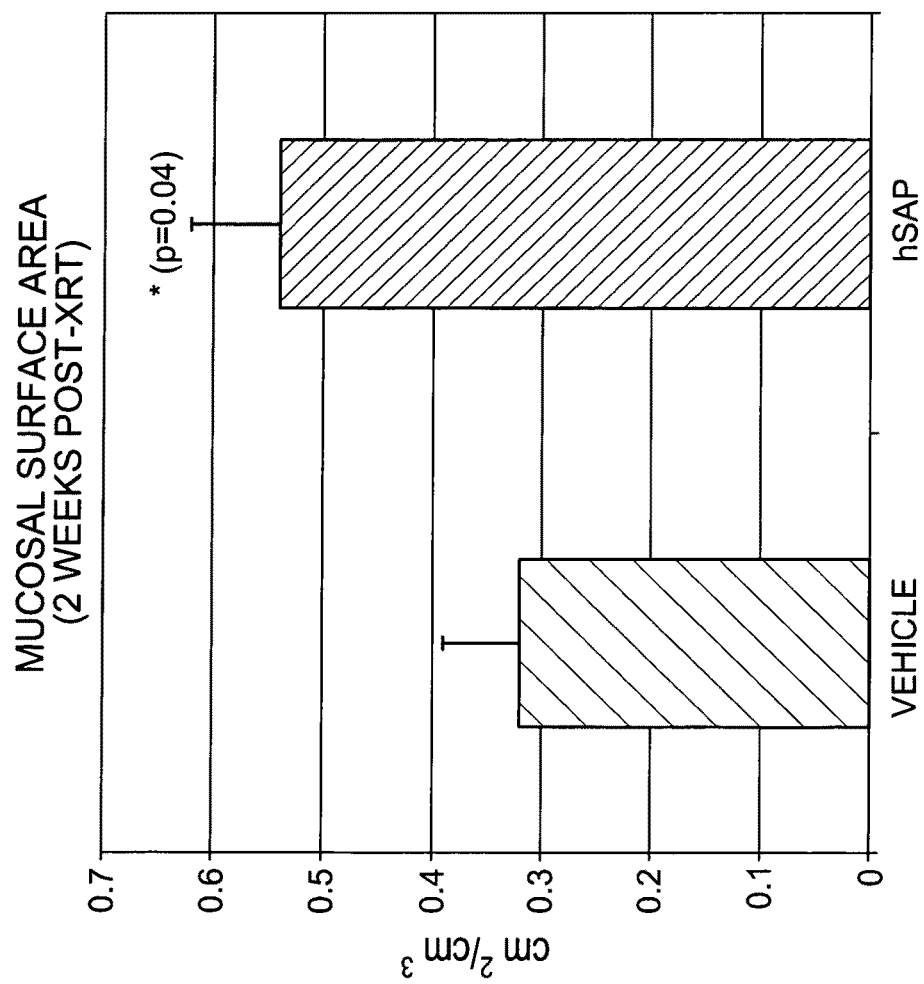
FIG. 2 depicts mucosal surface area two weeks after radiation treatment in hSAP-treated and in irradiated vehicle treated rats.
Figure 3:
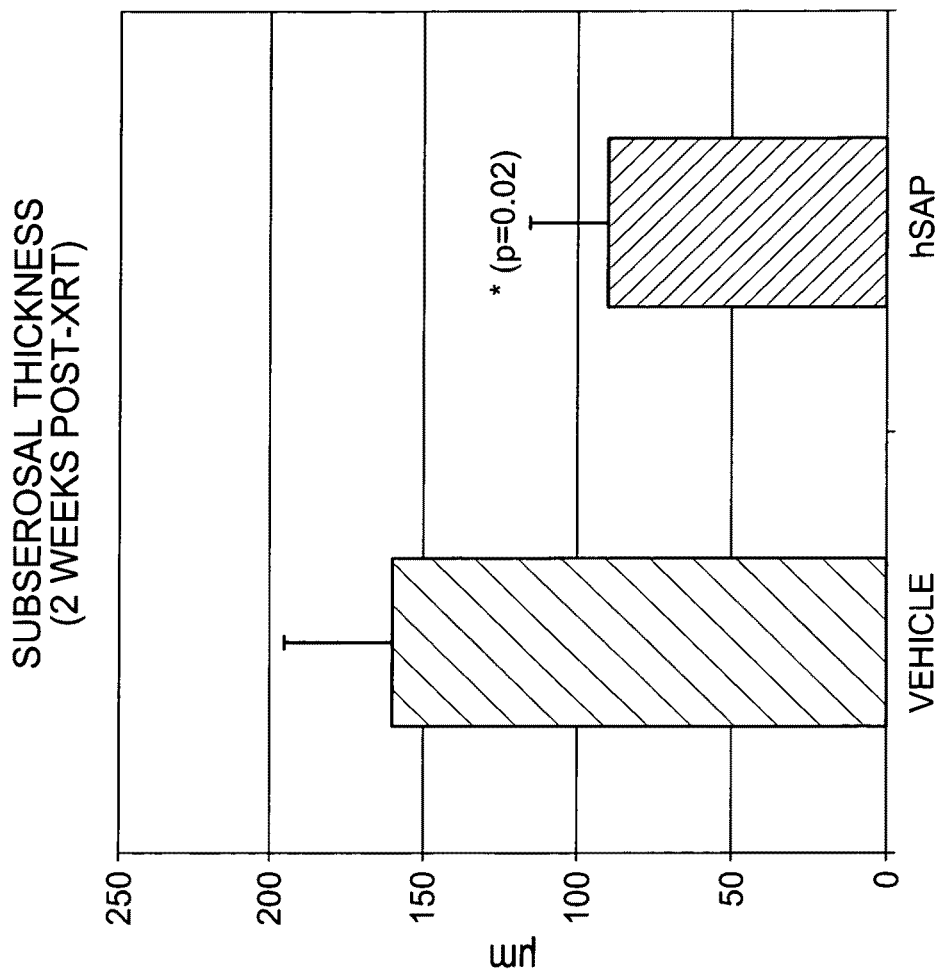
FIG. 3 depicts subserosal thickness two weeks after radiation treatment in hSAP-treated and in irradiated vehicle treated rats.
Figure 4:
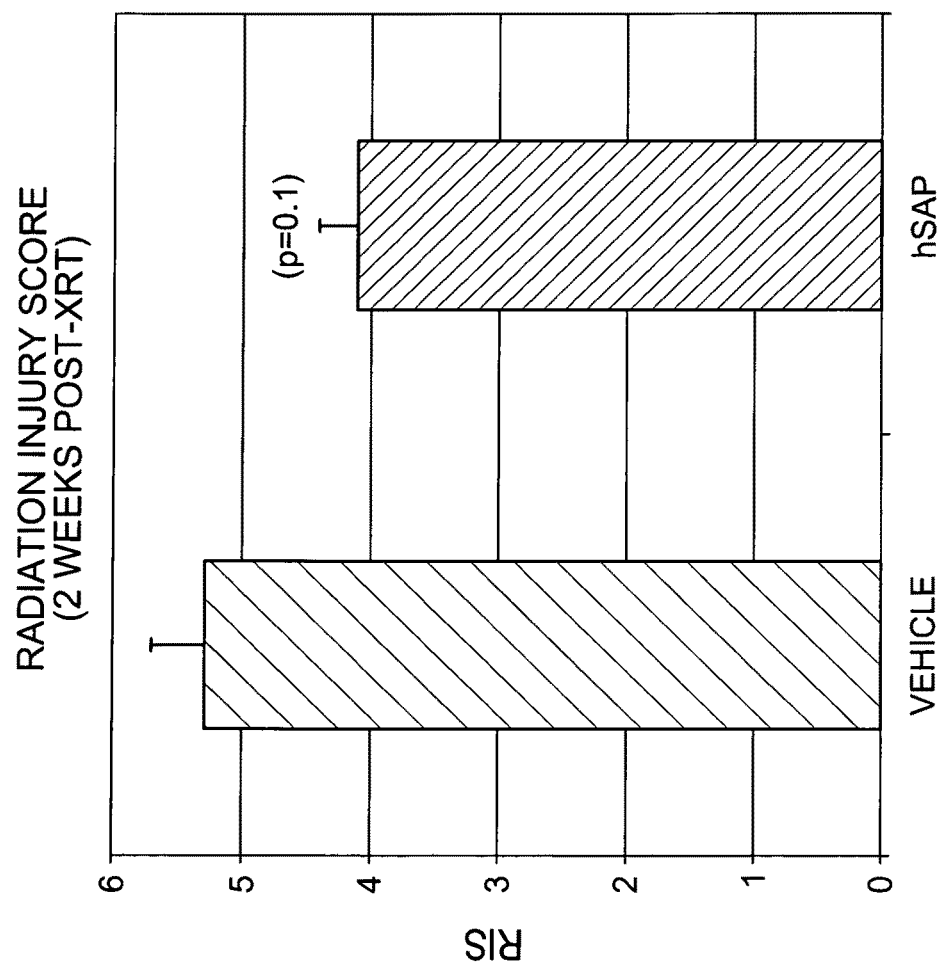
FIG. 4 depicts the radiation injury score two weeks after radiation treatment in hSAP-treated and in irradiated vehicle treated rats.
Figure 5:
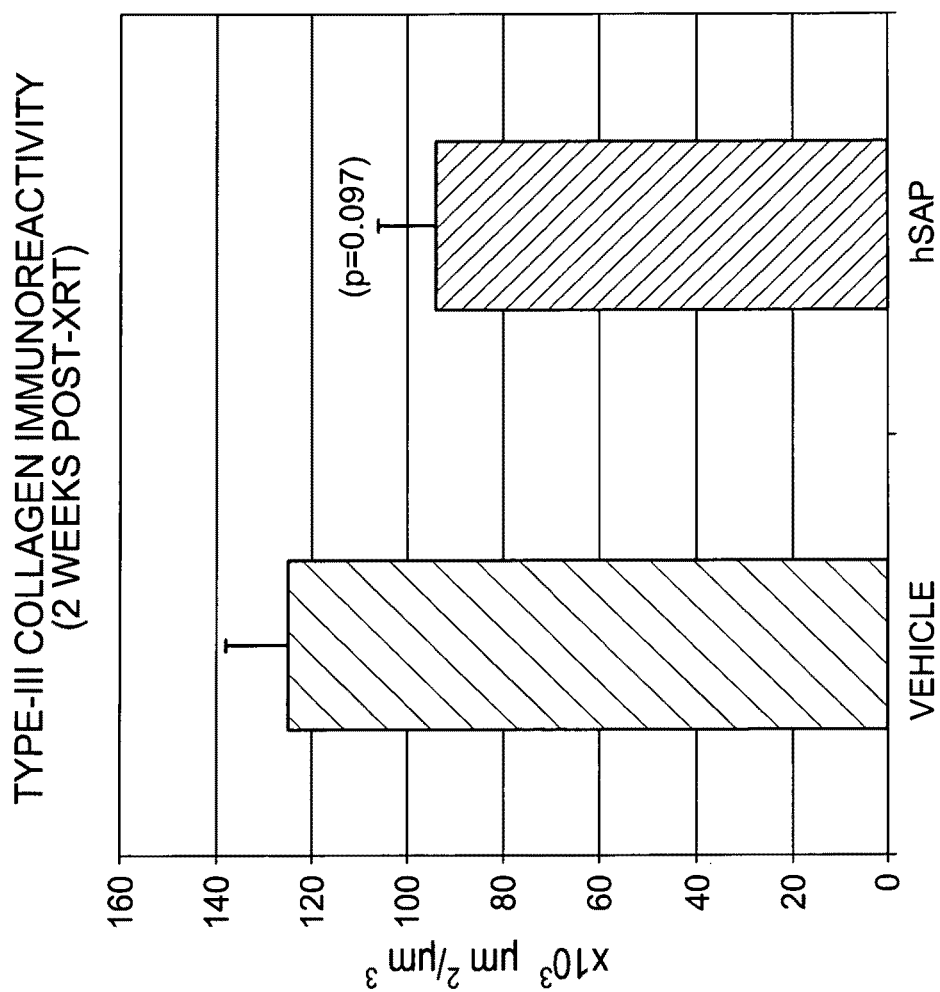
FIG. 5 depicts type-III collagen immunoreactivity two weeks after radiation treatment in hSAP-treated and in irradiated vehicle treated rats.

Hematoxylin and eosin (H&E) staining of intestines from non-irradiated control, irradiatated vehicle-treated and hSAP-treated rats are shown in FIG. 1. Epithelial atypia with abnormally oriented crypt cells, mucosal inflammation with areas of severe ulceration, reduced mucosal surface area, and significant subserosal thickening were observed in vehicle-treated animals. While mucosal damage and inflammation were evident in hSAP-treated animals, total mucosal surface area was significantly preserved (FIG. 2) and subserosal thickening was significantly reduced (FIG. 3). RIS was reduced in hSAP-treated animals (FIG. 4), but did not reach significance (p=0.1). Similarly, reduction of type-III collagen immunoreactivity (FIG. 5) did not reach significance (p=0.097).

Several parameters (vascular sclerosis, fibrosis including collagen deposition, lymphatic congestion and ileitis profunda) were used to calculate the radiation injury score developed during the intermediate (8 wk) and late periods (26 wk) of radiation enteropathy. The 14-day recovery period utilized in this current study did not allow for observation of these late-developing injuries. Extending recovery time beyond the acute injury phase is expected to increase the impact of SAP on both RIS and type-III collagen.

Hauer-Jensen, M., L. Poulakos, et al. (1988). "Effects of accelerated fractionation on radiation injury of the small intestine: a new rat model." *Int J Radiat Oncol Biol Phys* 14(6): 1205-12.

Hauer-Jensen, M., T. Sauer, et al. (1983). "Late changes following single dose roentgen irradiation of rat small intestine." *Acta Radiol Oncol* 22(4): 299-303.

Example 2

Human SAP (hSAP) was evaluated in a hamster cheek pouch model of radiation-induced oral mucositis (Sonis, 1990). Briefly, five- to six-week-old male Golden Syrian hamsters weighing 80-90 grams were exposed to a single 40 Gy dose of localized radiation on Day 0. Animals were anesthetized with IP ketamine/xylazine, the left buccal pouch was everted, and the rest of the body was protected with a lead shield. Radiation was generated with a 160 kilovolt potential source at a focal distance of 21 cm, hardened with a 3.0 mm Al filtration system, and delivered at a rate of 1.32 Gy/minute.

Hamsters (n=16/group) were dosed IP with vehicle (Group 1) or 2 mg/kg hSAP (Group 2) every other day beginning 30 minutes prior to radiation treatment for a total of 7 doses (final dose on Day 12). Eight additional animals (Group 3) served as age-matched controls (no radiation, no treatment).

Mucositis was evaluated clinically beginning on Day 6, continuing on alternate days until Day 28, then weekly until terminal sacrifice on Day 45. Animals were lightly anesthetized with inhaled anesthetic, and the left pouch was everted and photographed. At the end of the study, two blinded observers scored the photographs using a validated photographic scale (Sonis, 2000). A score ≧3 coincides with a clinically significant National Cancer Institute or World Health Organization score ≧3.

On Days 8 and 45, four hamsters from each study group were sacrificed and both buccal pouches were excised. On Days 16 and 28, four hamsters from groups 1 and 2 were sacrificed and both buccal pouches were excised. Pouches were fixed in 10% neutral buffered formalin and processed for histological evaluation. Slides were stained with H&E to examine fibrosis in the extracellular space. Slides were stained with Sirius red and analyzed with image analysis software to quantify total collagen deposition.

Figure 6:
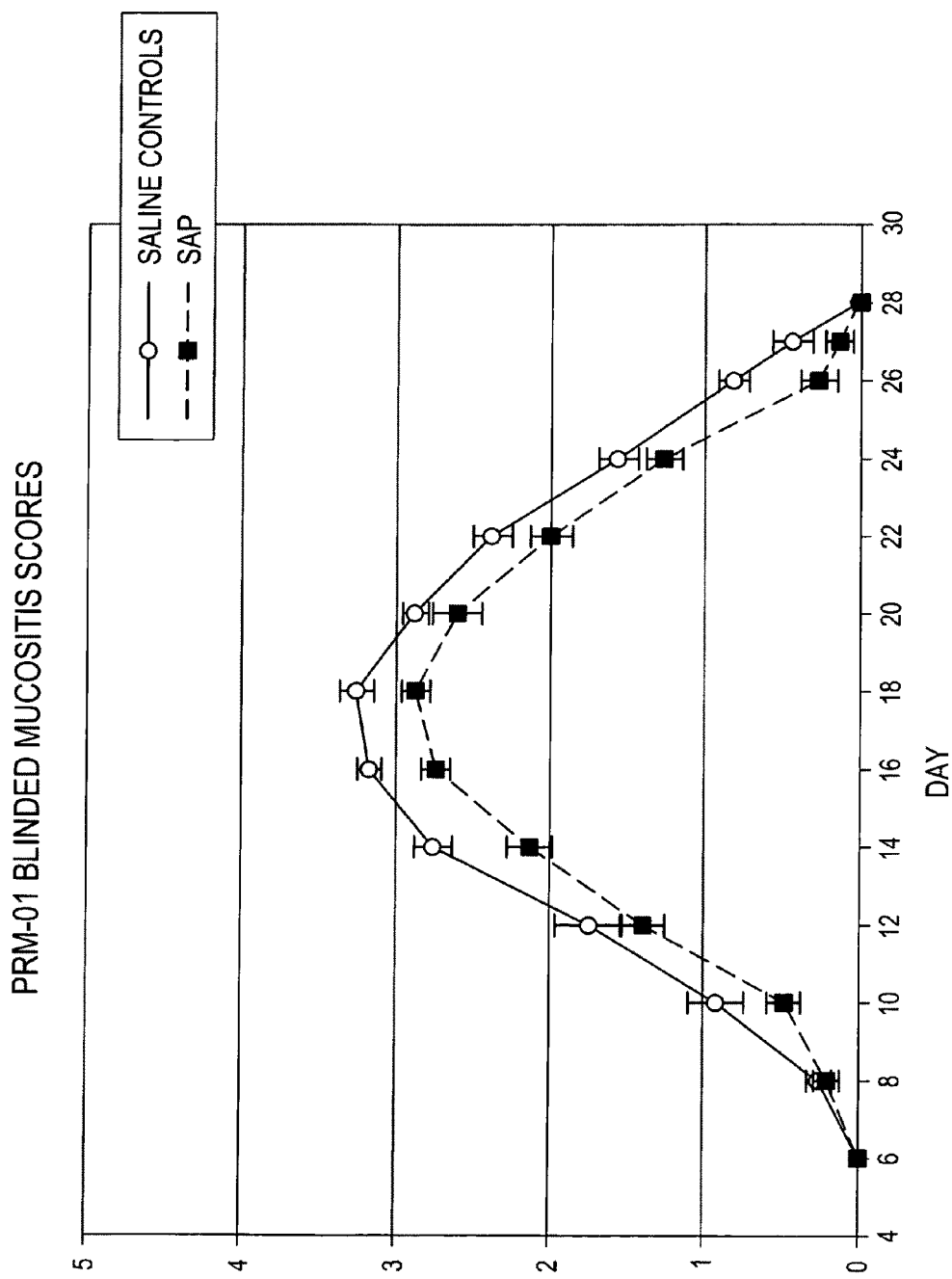
FIG. 6 depicts the mean blinded mucositis scores in a hamster cheek pouch model of radiation-induced oral mucositis.

The mean blinded mucositis scores are presented in FIG. 6. Mucositis peaked in the vehicle-treated animals on Day 18, with a mean score of 3.3. Both the day of peak effect and the mean peak score in vehicle-treated animals were consistent with historical data in this model. hSAP delayed the onset of mucositis and significantly reduced the mean peak score (2.9). The duration of mucositis, defined as the percentage of animal days spent with a score of ≦3, was significantly reduced in the hSAP-treated animals.

Sonis S T, Tracey C, Shklar G, Jenson J, Florine D. An animal model for mucositis induced by cancer chemotherapy. *Oral Surgery, Oral Medicine, Oral Pathology.* 69(4):437-43, 1990.

Sonis S T. Animal models of oral mucositis induced by antineoplastic drugs and radiation. In: Teicher B, ed. *Tumor models in cancer research.* Totowa, N.J.: Humana Press; 2000.

Example 3

Human SAP (hSAP) was evaluated in a hamster cheek pouch model of radiation-induced oral mucositis to examine the effects of dose schedule and dose level on the frequency, severity, and duration of oral mucositis. Following the same procedure outlined in Example 2, five- to six-week-old male Golden Syrian hamsters were irradiated on Day 0 with 40 Gy of localized radiation to the left cheek pouch. Hamsters (n=12/group) were dosed ip with vehicle or hSAP according to the following table 1:

TABLE 1

| Group Number | Treatment | Schedule |
|---|---|---|
| 1 | PBS, ip | Days 0, 2, 4, 6, 8, 10 & 12 |
| 2 | hSAP, ip, 2 mg/kg | Days −1, 0, 2, 4, 6, 8, 10 & 12, 16, 18, 20, 22, 24 & 26 |
| 3 | hSAP, ip, 2 mg/kg | Days 0, 1, 2, 3, 4, 5, 6, & 7 |
| 4 | hSAP, ip, 2 mg/kg | Days 0, 2, 4, 6, 8, 10 & 12 |
| 5 | hSAP, ip, 10 mg/kg | Days 0, 2, 4, 6, 8, 10 & 12 |

The Day 0 dose was administered 30 minutes prior to radiation. Mucositis was scored every other day beginning on Day 6, and continuing through Day 28, by anesthetizing the animals with an inhalation anesthetic and everting the cheek pouch. Mucositis was scored visually by comparison to a validated photographic scale, ranging from 0 for normal, to 5 for severe ulceration.

Figure 7:
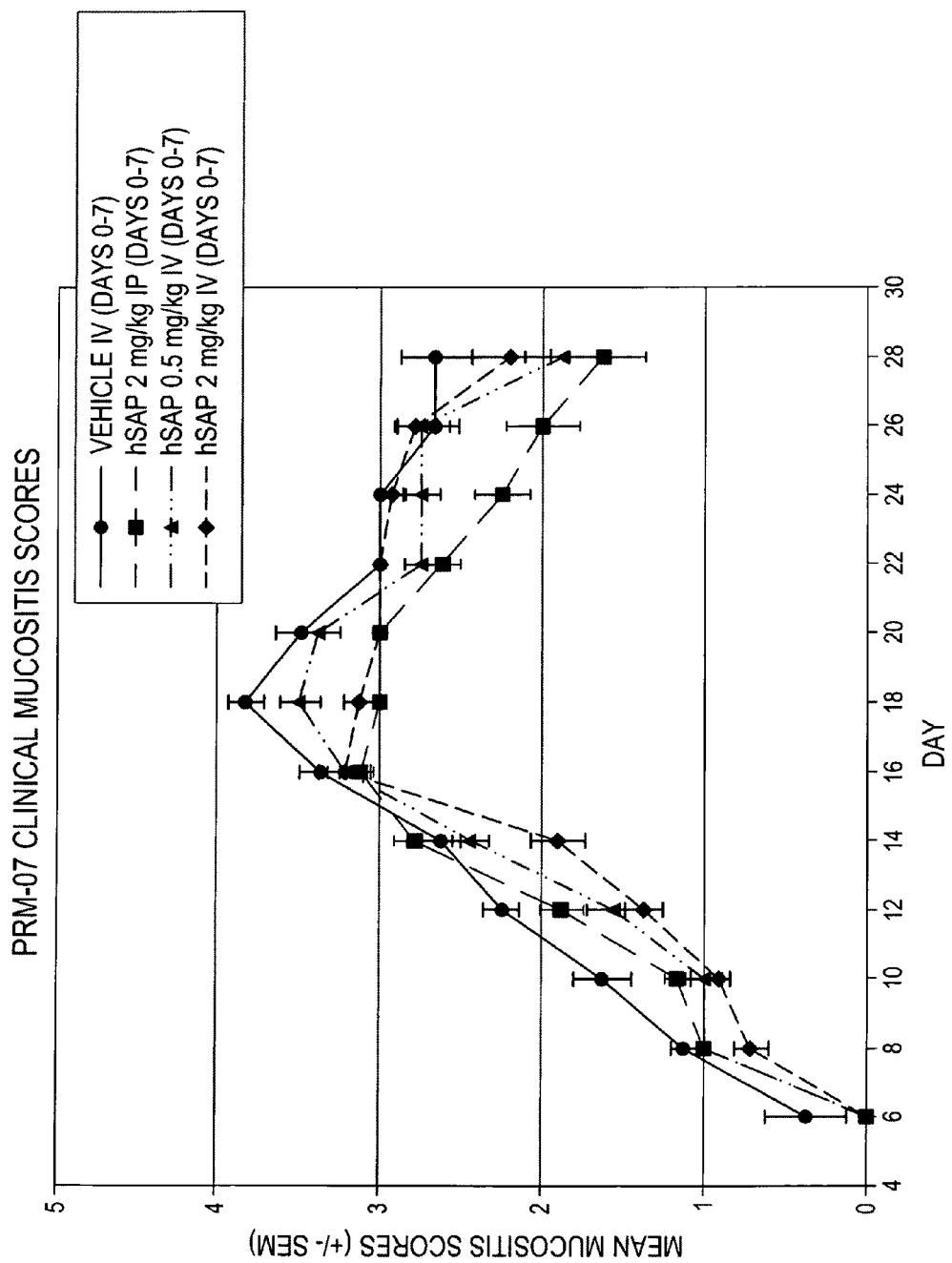
FIG. 7 depicts the mean blinded mucositis scores in hamster cheek pouch model of radition-induced oral mucositis.

The mean blinded mucositis scores are presented in FIG. 7. Mucositis peaked in the vehicle treated group on Day 14, with a mean score of 3.5. Groups treated with hSAP had a delayed and lowered peak of mucositis. Treatment effects on mucositis were also evaluated by calculating the number of days with a mucositis score of 3 or higher. Chi-squared analysis of these data showed that the percentage of days with a score of 3 or higher was significantly reduced in all groups treated with hSAP (Table 2).

TABLE 2

| Group Number | % Days with Mucositis Score ≥ 3 | P Value |
|---|---|---|
| 1 | 49.2 | — |
| 2 | 36.7 | 0.007 |
| 3 | 36.7 | 0.007 |
| 4 | 39.2 | 0.035 |
| 5 | 34.9 | 0.003 |

A further analysis of the mucositis scores was performed using the Mann-Whitney rank sum analysis to compare each hSAP treatment group to the vehicle control group. In this analysis, two days of significant reduction in the mucositis score are generally required before it is regarded as meaningful. Mucositis scores were significantly reduced on at least 4 days in all hSAP treatment groups relative to the vehicle control group (Table 3, significant differences identified in bold).

TABLE 3

| Group Number | Study Day | | | | | | | | | | | |
|---|---|---|---|---|---|---|---|---|---|---|---|---|
| | 6 | 8 | 10 | 12 | 14 | 16 | 18 | 20 | 22 | 24 | 26 | 28 |
| 2 | 0.217 | 0.018 | 0.039 | 0.252 | 0.056 | 0.101 | 0.297 | 0.297 | 0.232 | 0.299 | 0.030 | 0.029 |
| 3 | 0.626 | 0.374 | 0.934 | 0.403 | 0.026 | 0.269 | 0.135 | 0.280 | 0.061 | 0.002 | <0.001 | <0.001 |
| 4 | 0.217 | 0.021 | 0.006 | 0.287 | 0.003 | 0.048 | 0.230 | 0.116 | 0.072 | 0.461 | 0.030 | 0.003 |
| 5 | 0.138 | 0.010 | 0.061 | 0.285 | <0.001 | 0.149 | 0.138 | 0.250 | 0.137 | 0.518 | 0.021 | 0.006 |

In conclusion, all hSAP treatment groups had significant reductions in the number of days with a mucositis score of 3 or higher when compared to vehicle controls. Group 5 (10 mg/kg hSAP on Days 0-12, q2d) had the fewest number of days with a mucositis score of three or more (76 days compared to 118 days in the vehicle treated group, p=0.003). Group 4 (2 mg/kg hSAP on Days 0-12, q2d) exhibited the greatest overall reduction in daily mucositis scores as determined using the Mann-Whitney rank sum test.

Example 4

The effects of intravenous and intraperitoneal administration of hSAP were evaluated in a third study of radiation-induced oral mucositis. Hamsters in the intravenous dose groups were purchased with surgically implanted jugular catheters. Following the same procedure outlined in Example 2, five- to six-week-old male Golden Syrian hamsters were irradiated on Day 0 with 40 Gy of localized radiation to the left cheek pouch. Hamsters (n=12/group) were dosed with vehicle or hSAP according to the following table 4:

TABLE 4

| Group Number | Treatment | Schedule |
|---|---|---|
| 1 | PBS, iv | Days 0, 1, 2, 3, 4, 5, 6, & 7 |
| 2 | hSAP, ip, 2 mg/kg | Days 0, 1, 2, 3, 4, 5, 6, & 7 |
| 3 | hSAP, iv, 0.5 mg/kg | Days 0, 1, 2, 3, 4, 5, 6, & 7 |
| 4 | hSAP, ip, 2 mg/kg | Days 0, 1, 2, 3, 4, 5, 6, & 7 |

The Day 0 dose was administered 30 minutes prior to radiation. Mucositis was scored every other day beginning on Day 6, and continuing through Day 28, by anesthetizing the animals with an inhalation anesthetic and everting the cheek pouch. Mucositis was scored visually by comparison to a validated photographic scale, ranging from 0 for normal, to 5 for severe ulceration.

Figure 8:
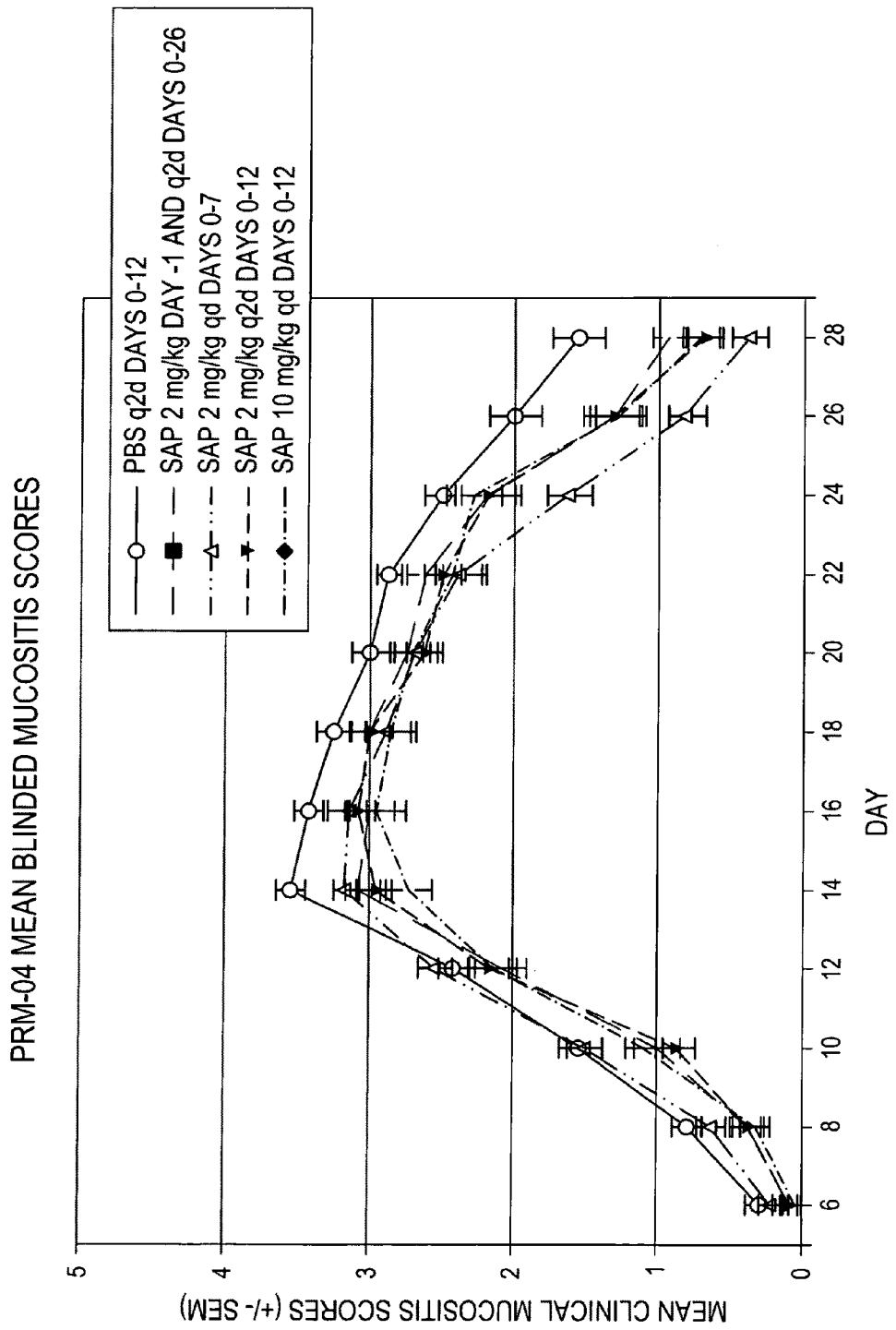
FIG. 8 depicts the mean blinded mucositis scores in hamster cheek pouch model of radiation-induced oral mucositis.

The mean blinded mucositis scores are presented in FIG. 8. Mucositis peaked in the vehicle treated group on Day 18, with a mean score of 3.8. The peak mucositis score was reduced in all hSAP treatment groups, although the day of peak effect was unchanged. Treatment effects on mucositis were also evaluated by calculating the number of days with a mucositis score of 3 or higher. Chi-squared analysis of these data showed that the percentage of days with a score of 3 or higher was significantly reduced in animals treated with ip hSAP, but was not significantly reduced in animals treated with iv hSAP (Table 5).

TABLE 5

| Group Number | % Days with Mucositis Score ≧ 3 | P Value |
|---|---|---|
| 1 | 57.1 | — |
| 2 | 43.3 | 0.008 |
| 3 | 50.0 | 0.204 |
| 4 | 46.8 | 0.056 |

A further analysis of the mucositis scores was performed using the Mann-Whitney rank sum analysis to compare each hSAP treatment group to the vehicle control group. In this analysis, two days of significant reduction in the mucositis score are generally required before it is regarded as meaningful. Mucositis score was significantly reduced in all groups treated with hSAP relative to the vehicle control group (Table 6, significant differences identified in bold).

TABLE 6

| Group Number | Study Day | | | | | | | | | | | |
|---|---|---|---|---|---|---|---|---|---|---|---|---|
| | 6 | 8 | 10 | 12 | 14 | 16 | 18 | 20 | 22 | 24 | 26 | 28 |
| 2 | 0.512 | 0.512 | 0.061 | 0.154 | 0.353 | 0.273 | <0.001 | 0.026 | 0.096 | 0.006 | 0.066 | 0.017 |
| 3 | 0.541 | 0.541 | 0.023 | 0.006 | 0.561 | 0.456 | 0.141 | 0.592 | 0.720 | 0.270 | 0.468 | 0.066 |
| 4 | 0.520 | 0.059 | 0.005 | <0.001 | 0.006 | 0.492 | 0.002 | 0.026 | 0.981 | 0.588 | 0.726 | 0.236 |

In conclusion, hamster treated with 2 mg/kg hSAP, ip had significant reductions in the number of days with a mucositis score of 3 or higher when compared to vehicle controls (p=0.008). This group showed statistically significant improvements relative to vehicle-treated controls on Days 18, 20, 24 and 28. Hamsters with implanted catheters (Groups 1, 3 & 4) had signs of infection at the catheter sites, which may have influenced the resolution of mucositis. Hamsters treated with iv hSAP did not show an improvement in the number of days with a mucositis score of 3 or higher, but the groups did show significant improvements relative to vehicle-treated controls on several study days.

We claim:

1. A method for treating, preventing or reducing the severity of mucositis in a patient, the method comprising administering, to a patient in need thereof, a therapeutically effective amount of Serum Amyloid P (SAP), wherein the SAP comprises protomers that are each at least 95% identical to the amino acid sequence of SEQ ID NO:1.

2. The method of claim 1, wherein administration of SAP delays the development of mucositis.

3. The method of claim 1, wherein administration of SAP reduces the number of days the patient is afflicted with mucositis.

4. The method of claim 1, wherein administration of SAP reduces the severity of mucositis by at least one grade, according to the National Cancer Institute-Common Toxicity Criteria.

5. The method of claim 1, wherein the mucositis is associated with radiation treatment, chemotherapy, or a combination thereof.

6. The method of claim 1, wherein the patient is at risk of developing mucositis.

7. The method of claim 6, wherein said administration commences prior to a treatment that places the patient at risk of developing mucositis.

8. The method of claim 6, wherein said administration commences concurrently with a treatment that places the patient at risk of developing mucositis.

9. The method of claim 6, wherein said administration commences after treatment that places the patient at risk of developing mucositis.

10. The method of claim 6, wherein the treatment that places the patient at risk of developing mucositis comprises radiation therapy, chemotherapy, or a combination thereof.

11. The method of any one of claims 1-10, wherein the patient is afflicted with cancer.

12. The method of any one of claims 1-10, wherein the patient is afflicted with head and neck, or breast, or lung or ovarian, prostate, or lymphatic, leukemic or gastrointestinal cancer.

13. The method of any one of claims 1-10, wherein the mucositis is oral mucositis.

14. The method of any one of claims 1-10, wherein the mucositis is gastrointestinal mucositis.

15. The method of any one of claims 1-10, wherein the mucositis is alimentary mucositis.

16. The method of any one of claims 1-10, wherein the mucositis is esophageal mucositis.

17. The method of claim 1, wherein the SAP increases SAP signaling.

18. The method of claim 1, wherein the SAP mimics SAP signaling.

19. The method of claim 1, wherein the SAP increases SAP activity.

20. The method of claim 1, further comprising administering a therapeutically effective amount of velafermin.

21. The method of claim 1, further comprising administering a therapeutically effective amount of palifermin.

22. The method of claim 1, wherein the SAP comprises protomers that are each at least 97% identical to the amino acid sequence of SEQ ID NO:1.

23. The method of claim 1, wherein the SAP comprises protomers that are each at least 99% identical to the amino acid sequence of SEQ ID NO:1.

24. The method of claim 1, wherein the SAP comprises protomers that each have the amino acid sequence of SEQ ID NO:1.

* * * * *

SEQUENCE LISTING

<160> NUMBER OF SEQ ID NOS: 4

<210> SEQ ID NO 1
<211> LENGTH: 204
<212> TYPE: PRT
<213> ORGANISM: Homo sapiens

<400> SEQUENCE: 1

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Asn
            20                  25                  30

Phe Thr Leu Cys Phe Arg Ala Tyr Ser Asp Leu Ser Arg Ala Tyr Ser
        35                  40                  45

Leu Phe Ser Tyr Asn Thr Gln Gly Arg Asp Asn Glu Leu Leu Val Tyr
    50                  55                  60

Lys Glu Arg Val Gly Glu Tyr Ser Leu Tyr Ile Gly Arg His Lys Val
65                  70                  75                  80

Thr Ser Lys Val Ile Glu Lys Phe Pro Ala Pro Val His Ile Cys Val
                85                  90                  95

Ser Trp Glu Ser Ser Ser Gly Ile Ala Glu Phe Trp Ile Asn Gly Thr

```
                100             105             110
Pro Leu Val Lys Lys Gly Leu Arg Gln Gly Tyr Phe Val Glu Ala Gln
        115                 120                 125

Pro Lys Ile Val Leu Gly Gln Glu Gln Asp Ser Tyr Gly Gly Lys Phe
130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
                180                 185                 190

Arg Gly Tyr Val Ile Ile Lys Pro Leu Val Trp Val
        195                 200

<210> SEQ ID NO 2
<211> LENGTH: 208
<212> TYPE: PRT
<213> ORGANISM: Gallus gallus

<400> SEQUENCE: 2

Gln Glu Asp Leu Tyr Arg Lys Val Phe Val Phe Arg Glu Asp Pro Ser
1               5                   10                  15

Asp Ala Tyr Val Leu Leu Gln Val Gln Leu Glu Arg Pro Leu Leu Asn
                20                  25                  30

Phe Thr Val Cys Leu Arg Ser Tyr Thr Asp Leu Thr Arg Pro His Ser
            35                  40                  45

Leu Phe Ser Tyr Ala Thr Lys Ala Gln Asp Asn Glu Ile Leu Leu Phe
        50                  55                  60

Lys Pro Lys Pro Gly Glu Tyr Arg Phe Tyr Val Gly Gly Lys Tyr Val
65                  70                  75                  80

Thr Phe Arg Val Pro Glu Asn Arg Gly Glu Trp Glu His Val Cys Ala
                85                  90                  95

Ser Trp Glu Ser Gly Ser Gly Ile Ala Glu Phe Trp Leu Asn Gly Arg
                100                 105                 110

Pro Trp Pro Arg Lys Gly Leu Gln Lys Gly Tyr Glu Val Gly Asn Glu
        115                 120                 125

Ala Val Val Met Leu Gly Gln Glu Gln Asp Ala Tyr Gly Gly Gly Phe
130                 135                 140

Asp Val Tyr Asn Ser Phe Thr Gly Glu Met Ala Asp Val His Leu Trp
145                 150                 155                 160

Asp Ala Gly Leu Ser Pro Asp Lys Met Arg Ser Ala Tyr Leu Ala Leu
                165                 170                 175

Arg Leu Pro Pro Ala Pro Leu Ala Trp Gly Arg Leu Arg Tyr Glu Ala
                180                 185                 190

Lys Gly Asp Val Val Lys Pro Arg Leu Arg Glu Ala Leu Gly Ala
        195                 200                 205

<210> SEQ ID NO 3
<211> LENGTH: 205
<212> TYPE: PRT
<213> ORGANISM: Bos taurus

<400> SEQUENCE: 3

Gln Thr Asp Leu Arg Gly Lys Val Phe Val Phe Pro Arg Glu Ser Ser
1               5                   10                  15

Thr Asp His Val Thr Leu Ile Thr Lys Leu Glu Lys Pro Leu Lys Asn
                20                  25                  30
```

```
Leu Thr Leu Cys Leu Arg Ala Tyr Ser Asp Leu Ser Arg Gly Tyr Ser
             35                  40                  45

Leu Phe Ser Tyr Asn Ile His Ser Lys Asp Asn Glu Leu Leu Val Phe
 50                      55                  60

Lys Asn Gly Ile Gly Glu Tyr Ser Leu Tyr Ile Gly Lys Thr Lys Val
 65                  70                  75                  80

Thr Val Arg Ala Thr Glu Lys Phe Pro Ser Pro Val His Ile Cys Thr
                 85                  90                  95

Ser Trp Glu Ser Ser Thr Gly Ile Ala Glu Phe Trp Ile Asn Gly Lys
                100                 105                 110

Pro Leu Val Lys Arg Gly Leu Lys Gln Gly Tyr Ala Val Gly Ala His
            115                 120                 125

Pro Lys Ile Val Leu Gly Gln Glu Gln Asp Ser Tyr Gly Gly Gly Phe
        130                 135                 140

Asp Lys Asn Gln Ser Phe Met Gly Glu Ile Gly Asp Leu Tyr Met Trp
145                 150                 155                 160

Asp Ser Val Leu Ser Pro Glu Glu Ile Leu Val Tyr Gln Gly Ser
                165                 170                 175

Ser Ser Ile Ser Pro Thr Ile Leu Asp Trp Gln Ala Leu Lys Tyr Glu
            180                 185                 190

Ile Lys Gly Tyr Val Ile Val Lys Pro Met Val Trp Gly
        195                 200                 205

<210> SEQ ID NO 4
<211> LENGTH: 204
<212> TYPE: PRT
<213> ORGANISM: Cricetulus migratorius

<400> SEQUENCE: 4

Gln Thr Asp Leu Thr Gly Lys Val Phe Val Phe Pro Arg Glu Ser Glu
 1               5                  10                  15

Ser Asp Tyr Val Lys Leu Ile Pro Arg Leu Glu Lys Pro Leu Glu Asn
                 20                  25                  30

Phe Thr Leu Cys Phe Arg Thr Tyr Thr Asp Leu Ser Arg Pro His Ser
             35                  40                  45

Leu Phe Ser Tyr Asn Thr Lys Asn Lys Asp Asn Glu Leu Leu Ile Tyr
 50                      55                  60

Lys Glu Arg Met Gly Glu Tyr Gly Leu Tyr Ile Glu Asn Val Gly Ala
 65                  70                  75                  80

Ile Val Arg Gly Val Glu Phe Ala Ser Pro Val His Phe Cys Thr
                 85                  90                  95

Ser Trp Glu Ser Ser Gly Ile Ala Asp Phe Trp Val Asn Gly Ile
                100                 105                 110

Pro Trp Val Lys Lys Gly Leu Lys Lys Gly Tyr Thr Val Lys Thr Gln
            115                 120                 125

Pro Ser Ile Ile Leu Gly Gln Glu Gln Asp Asn Tyr Gly Gly Gly Phe
        130                 135                 140

Asp Lys Ser Gln Ser Phe Val Gly Glu Met Gly Asp Leu Asn Met Trp
145                 150                 155                 160

Asp Ser Val Leu Thr Pro Glu Glu Ile Lys Ser Val Tyr Glu Gly Ser
                165                 170                 175
```

```
Trp Leu Glu Pro Asn Ile Leu Asp Trp Arg Ala Leu Asn Tyr Glu Met
            180                 185                 190

Ser Gly Tyr Ala Val Ile Arg Pro Arg Val Trp His
            195                 200
```